US010625101B2

(12) United States Patent
Klingelmeyer et al.

(10) Patent No.: US 10,625,101 B2
(45) Date of Patent: Apr. 21, 2020

(54) METHOD FOR COLOURING HAIR

(75) Inventors: Annette Elsbeth Klingelmeyer, Darmstadt (DE); Thomas Krause, Darmstadt (DE); Uwe Mahla, Gross Bieberau (DE); Knut Meinert, Lampertheim (DE); Matthias Morand, Bad Soden (DE); Manfred Schmitt, Bensheim (DE); Maik Tremel, Schwalbach (DE); Elizabeth Ana Diez McCready, San Sebastiàn (ES)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 13/610,232

(22) Filed: Sep. 11, 2012

(65) Prior Publication Data

US 2013/0061866 A1    Mar. 14, 2013

(30) Foreign Application Priority Data

Sep. 12, 2011   (EP) ..................... 11180863

(51) Int. Cl.
*A61Q 5/06* (2006.01)
*A61K 8/81* (2006.01)
*A61Q 5/10* (2006.01)
*A61K 8/87* (2006.01)
*A61K 8/03* (2006.01)

(52) U.S. Cl.
CPC .................. *A61Q 5/06* (2013.01); *A61K 8/03* (2013.01); *A61K 8/8152* (2013.01); *A61K 8/87* (2013.01); *A61Q 5/10* (2013.01); *A61K 2800/48* (2013.01)

(58) Field of Classification Search
None
See application file for complete search history.

(56) References Cited

U.S. PATENT DOCUMENTS

| | | | | |
|---|---|---|---|---|
| 6,190,647 | B1 * | 2/2001 | Karlen ................ | A61K 8/8152 132/202 |
| 6,423,101 | B1 | 7/2002 | Yaker | |
| 7,364,594 | B2 | 4/2008 | Cottard et al. | |
| 7,481,846 | B2 * | 1/2009 | Marsh ...................... | A61K 8/22 132/202 |
| 7,591,862 | B2 | 9/2009 | Schmenger et al. | |
| 2002/0157191 | A1 * | 10/2002 | Casperson et al. ............... | 8/405 |
| 2003/0049224 | A1 * | 3/2003 | Birkel ................... | A61K 8/042 424/70.16 |
| 2004/0055094 | A1 * | 3/2004 | Massoni ................ | A61K 8/416 8/405 |
| 2004/0065338 | A1 * | 4/2004 | Colacioppo ............ | A45D 19/02 132/126 |
| 2004/0089316 | A1 | 5/2004 | Hamilton et al. | |
| 2005/0232886 | A1 | 10/2005 | Walter et al. | |
| 2006/0079422 | A1 | 4/2006 | Midha et al. | |
| 2006/0134049 | A1 * | 6/2006 | Keenan et al. ............ | 424/70.15 |
| 2007/0009463 | A1 | 1/2007 | Niebauer | |
| 2007/0224145 | A1 * | 9/2007 | Walter et al. ................ | 424/70.6 |
| 2008/0083420 | A1 * | 4/2008 | Glenn et al. .................. | 132/208 |
| 2008/0087293 | A1 * | 4/2008 | Glenn ................ | A45D 19/0008 132/210 |
| 2008/0189876 | A1 * | 8/2008 | Trigg ..................... | A61K 8/585 8/405 |
| 2008/0196174 | A1 | 8/2008 | Schmenger | |
| 2009/0119852 | A1 * | 5/2009 | Marsh .............................. | 8/408 |
| 2011/0117225 | A1 | 5/2011 | Wei et al. | |

FOREIGN PATENT DOCUMENTS

| | | |
|---|---|---|
| CA | 2235477 C | 10/2001 |
| CN | 101616713 A | 12/2009 |
| DE | 29923520 U1 | 10/2000 |
| EP | 1294343 B1 | 8/2005 |
| EP | 1889606 A1 | 2/2008 |
| EP | 1961450 A1 | 8/2008 |
| EP | 2338470 A1 | 6/2011 |
| JP | 02-076807 A | 3/1990 |
| JP | 10-316546 A | 12/1998 |
| JP | 2005-306868 A | 11/2005 |
| JP | 2006-509741 A | 3/2006 |
| JP | 2006347966 A * | 12/2006 |

(Continued)

OTHER PUBLICATIONS blog.freepeople.com article "The rainbow braid," dated Sep. 9, 2010: http://blog.freepeople.com/2010/09/the-rainbow-braid/.*
Folica.com product information page for "manic panic" hair coloring styling gel, printed 2014; http://www.folica.com/reviews/hair-color/temporary-hair-coloring/manic-panic-dyehard-temporary-hair-color-styling-gel.*
Dow's product information sheet for Aculyn™ 28 dated Feb. 2004.*
Machine translation, WO 2011-020646, printed 2016.*
Vetrano "Zach's Wax extreme color gel—hair coloring fun," available online Oct. 23, 2010; https://www.shescribes.com/zachs-wax-hair-coloring-fun/.*
Google date, "Zach's Wax extreme color gel—hair coloring fun," printed 2019.*
Machine translation JP 2006-347966, printed 2019.*
Clairol "Advanced highlighting methods," available online Jan. 15, 2010; https://www.clairolpro.com/inside-clairol-pro/advanced-highlighting-methods.*

(Continued)

*Primary Examiner* — David J Blanchard
*Assistant Examiner* — Alissa Prosser
(74) *Attorney, Agent, or Firm* — Schwegman Lundberg & Woessner, P.A.

(57) ABSTRACT

A method for colouring hair, wherein the method comprises: (i) the formation of a first plurality of coated hair fibre portions, wherein the coating comprises a first composition, wherein the first composition comprises a first hair colouring agent, a hydrophobic phase, a hydrophilic phase, a surfactant, and a thickener capable of interacting with the hydrophobic phase and the hydrophilic phase; and subsequently (ii) styling the hair wherein the first plurality of coated hair fibre portions is contacted with a second plurality of hair fibre portions; wherein the method does not comprise the application of a solid barrier means in order to separate the first plurality of coated hair fibre portions from the second plurality of hair fibre portions, and wherein the first composition is substantially free of persulfate.

12 Claims, 18 Drawing Sheets

(56) References Cited

FOREIGN PATENT DOCUMENTS

| WO | WO-2004/041020 A2 | 5/2004 | | |
|---|---|---|---|---|
| WO | WO-2008116147 A2 | 9/2008 | | |
| WO | WO 2009/153280 | * | 12/2009 | |
| WO | WO 2011020646 A2 | * | 2/2011 | A61K 8/925 |
| WO | WO 2011/076358 | * | 6/2011 | |

OTHER PUBLICATIONS

Google date "Advanced highlighting methods," printed 2019.*
Hydrophobic Oxidative Hair Dye 8781-58; 2 pages, Feb. 11, 2002.
Cosmetic and Dermatologic Formulations Containing the Polymeric Rheology Modifier Polyurethane-39; 125 pages/5 parts, Jun. 8, 2009.
GNPD database; Mintel; Heads Up! Couture Highlighting Kit; 11 pages, Sep. 2009.
"ACULYN tm 28 Rheology Modifier / Stabilizer Data Sheet", (c)Rohm and Haas, 2006, (2006), 11 pgs.
"Chinese Application Serial No. 201280043900.3, Office Action dated Jan. 14, 2016", (w/ English Abstract), 8 pgs.
"Chinese Application Serial No. 201280043900.3, Office Action dated Jul. 6, 2016", (w/ English Translation), 7 pgs.
"Chinese Application Serial No. 201280043900.3, Office Action dated Aug. 10, 2015", (w/ English Translation), 14 pgs.
"Chinese Application Serial No. 201280043900.3, Office Action dated Dec. 9, 2014", (w/ English Translation), 15 pgs.
"Chinese Application Serial No. 201280043900.3, Response filed Mar. 9, 2016 to Office Action dated Jan. 14, 2016", 4 pgs.
"Chinese Application Serial No. 201280043900.3, Response filed Apr. 13, 2015 to Office Action dated Dec. 9, 2014", (w/English Translation of Argument), 6 pgs.
"Chinese Application Serial No. 201280043900.3, Response filed Sep. 12, 2016 to Office Action dated Jul. 6, 2016", 4 pgs.
"Chinese Application Serial No. 201280043900.3, Response filed Oct. 9, 2015 to Office Action dated Aug. 10, 2015", 6 pgs.
"European Application Serial No. 15156306.1, Extended European Search Report dated Jun. 15, 2015", 7 pgs.
"European Application Serial No. 15156303.1, Response filed Jan. 27, 2016 to Extended European Search Report dated Jun. 15, 2015", 12 pgs.
"Mexican Application Serial No. MX/a/2014/002862, Office Action dated Aug. 12, 2016", 1 pg.
"European Application Serial No. 12183832.0, Partial European Search Report dated Feb. 6, 2013", 7 pgs.
"European Application Serial No. 12183832.0, Response filed Feb. 12, 2015 to extended European Search Report dated Jul. 25, 2014", 12 pgs.
"European Application Serial No. 15156306.1, Office Action dated Jul. 20, 2017", 6 pgs.
"Mexican Application Serial No. MX/a/2014/002862, Response filed Jun. 5, 2017 to Office Action dated Feb. 27, 2017", evv/ English Translation of Claims), 16 pgs.
"European Application Serial No. 12183832.0, extended European Search Report dated Jul. 25, 2014", 14 pgs.
"European Application Serial No. 12183832.0, Office Action dated Mar. 2, 2016", 6 pgs.
"European Application Serial No. 12183832.0, Office Action dated May 5, 2015", 7 pgs.
"European Application Serial No. 12183832.0, Office Action dated Sep. 1, 2014", 2 pgs.
"European Application Serial No. 12183832.0, Reply filed Nov. 16, 2015 to Office Action dated May 5, 2015", 9 pgs.
"European Application Serial No. 12183832.0, Response filed Feb. 15, 2015 to Office Action dated Sep. 1, 2014", 13 pgs.
"International Application Serial No. PCT/US2012/054621, International Preliminary Report on Patentability dated Mar. 20, 2014", 12 pgs.
"International Application Serial No. PCT/US2012/054621, International Search Report dated Jan. 17, 2014", 6 pgs.
"International Application Serial No. PCT/US2012/054621, Written Opinion dated Jan. 17, 2014", 10 pgs.
"Japanese Application Serial No. 2014-529966, Notification dated Apr. 28, 2015", (W/ English Translation), 9 pgs.
"Japanese Application Serial No. 2014-529966, Written Argument and Amendment filed Jul. 22, 2015 in response to Notification dated Apr. 28, 2015", (w/ English Translation), 16 pgs.
"Mexican Application Serial No. MX/a/2014/002862, Office Action dated Feb. 27, 2017", (w/ English Summary), 3 pgs.
"Mexican Application Serial No. MX/a/2014/002862, Office Action dated Aug. 24, 2017", (w/ English Summary), 4 pgs.
"Mexican Application Serial No. MX/a/2014/002862, Response filed Nov. 11, 2017 to Office Action dated Aug. 24, 2017", (w/ English Translation of Claims), 12 pgs.
"European Application Serial No. 12183832.0, Communication Pursuant to Article 94(3) EPC dated Apr. 24, 2018", 5 pgs.
"European Application Serial No. 12183832.0, Response filed Jul. 24, 2018 to Office Action dated May 5, 2015", w/ English Claims, 9 pgs.
"European Application U.S. Serial No. 12183832.0, Response filed Apr. 17, 2019 to Communication Pursuant to Article 94(3) EPC dated Feb. 25, 2019", 16 pgs.
"European Application Serial No. 12183832.0, Communication Pursuant to Article 94(3) EPC dated Feb. 25, 2019", 5 pgs.

* cited by examiner

METHOD FOR COLOURING HAIR

FIELD OF THE INVENTION

A method for colouring hair, wherein the method comprises: the formation of a first plurality of coated hair fibre portions using a hair colouring agent, a hydrophobic phase, a hydrophilic phase, a surfactant, and a thickener capable of interacting with the hydrophobic phase and the hydrophilic phase; and subsequently styling the hair.

BACKGROUND OF THE INVENTION

Hair colouring or dyeing involves the application of a hair dye onto hair which results in the colouration of hair fibres. Typically the hair colour is changed or 'freshened up'. In highlighting, a limited number of sections of the head of hair—typically a plurality of hair fibres from their route to tip—are dyed to a lighter hair colour, wherein the sections are spaced out at intervals such that undyed sections remain inbetween. Lowlighting is a similar procedure wherein a darker colour dye is utilised instead. The hair can also be highlighted with other colours e.g. red and/or purple tones. The entire head of hair can be dyed using this method e.g. with 3 different hair colouring agents for a more striking look. The end result is normally increased appearance of texture and vibrancy of the hair. The dyeing can also be tailored to the final hairstyle in order to highlight certain aspects or draw attention away from other features. Subtle highlighting/lowlighting can give the impression of a slight lightening/darkening of the hair shade and results in a fresher look.

Highlighting (and lowlighting) typically employs the use of barrier means, such as foils, in order to prevent bundles of hair fibres intentionally treated with a hair colouring agent from contacting other hair fibres and thus transfer of the hair colouring agent onto hair fibres that were not intended to be coloured at all or intended to be coloured with a different dye. Coloured fibres when contacted with other hair fibres can transfer their dye onto these other fibres, which are then also dyed—this is sometimes known as 'staining'. Therefore, barrier means are used to wrap up each intentionally dyed bundle of hair fibres and thus separate it from the other hair fibres. The wrapped bundles are then typically left to develop for a period of time before the hair dye is rinsed out and the final cut and style carried out.

There is a need, however, for the consumer to feel more beautiful during the hair dyeing process—some consumers believe that it detracts from this when they have to spend a period of time in the hairdressing salon with their head covered in e.g. foil parcels. Moreover, there is a need for speeding up the process of dyeing hair. Furthermore, there is a need for providing the stylist with greater artistic and creative freedom, vis-à-vis the relationship of the hair colour and the final hairstyle, during the application of the dye and during the dye development time. There is also a need for reducing the use of solid barrier means e.g. foils, such as for environmental reasons e.g. reduction of waste. Furthermore, there is a need to provide the consumer with a means to highlight/lowlight their hair by themselves i.e. at home without the need for a stylist.

In summary, there is a constant need for providing methods resulting in improved efficiency, flexibility and freedom for the stylist. There is a need for the consumer to have an improved feeling of well-being and beautification during the entire process of hair colouring and not just after treatment, and for the process to be quicker. There is a need for the stylists to be able to envision, create and experiment with the final look at every stage throughout the colouring process.

SUMMARY OF THE INVENTION

According to the first aspect, the invention relates to a method for colouring hair, wherein the method comprises:
  (i) the formation of a first plurality of coated hair fibre portions, wherein the coating comprises a first composition, wherein the first composition comprises a first hair colouring agent, a hydrophobic phase, a hydrophilic phase, a surfactant, and a thickener capable of interacting with the hydrophobic phase and the hydrophilic phase; and subsequently
  (ii) styling the hair wherein the first plurality of coated hair fibre portions is contacted with a second plurality of hair fibre portions;
wherein the method does not comprise the application of a solid barrier means in order to separate the first plurality of coated hair fibre portions from the second plurality of hair fibre portions; wherein the first composition is substantially free of persulfate.

According to a second aspect, the present invention relates to a composition for colouring hair comprising a hair colouring agent, a hydrophobic phase, a hydrophilic phase, a surfactant, and a thickener capable of interacting with the hydrophobic phase and the hydrophilic phase, wherein the composition has a storage modulus of at least about 3000 Pa, or at least about 3300 Pa, or at least about 3500 Pa, or at least about 4000 Pa, or at least about 4500 Pa, or at least about 5000 Pa, measured by frequency sweep at an angular frequency of 0.6 rad/s at 23° C., and wherein the thickener is an associative thickening polymer and comprises hydrophobic moieties and hydrophilic moieties.

According to a third aspect, the present invention relates to the use of the composition according to the second aspect, for colouring and/or styling hair.

According to a fourth aspect, the present invention relates to a kit comprising: (a) application instructions comprising the method according to the first aspect; (b) a composition.

According to a fifth aspect, the present invention relates to a process for creating a composition for colouring hair comprising mixing: a hair colouring agent; a hydrophobic phase; a hydrophilic phase; a surfactant; and a thickener capable of interacting with the hydrophobic phase and the hydrophilic phase; wherein the composition has a storage modulus of at least about 3000 Pa, or at least about 3300 Pa, or at least about 3500 Pa, or at least about 4000 Pa, or at least about 4500 Pa, or at least about 5000 Pa, measured by frequency sweep at an angular frequency of 0.6 rad/s at 23° C.

According to a sixth aspect, the present invention relates to a method for demonstrating the immiscibility of two or more liquids, wherein each liquid exhibits a different colour, the method comprising:
  a. providing a first colour formulation, wherein the first colour formulation comprises a hydrophilic phase, a first colourant and an alkalising agent;
  b. providing a second colour formulation, wherein the second formulation comprises a hydrophilic phase, a second colourant and an alkalising agent;
  c. providing a thickening formulation, wherein the thickening formulation comprises thickener capable of interacting with the hydrophobic phase and capable of undergoing hydrophobic-hydrophobic interactions;
  d. mixing the first formulation with the thickening formulation to form a first liquid exhibiting a first colour and mixing the second formulation with the thickening formulation to form a second liquid exhibiting a second colour; and subsequently e. applying the first liquid and second liquid next to each other in or on a receptacle; and subsequently
f. agitating the receptacle; and subsequently
g. observing the immiscibility of the first liquid and the second liquid;
h. optionally comparing said receptacle with a control demonstration where said liquids are substantially free of said thickener.

According to a seventh aspect, the present invention relates to a thickening formulation comprising: an oxidising agent, and an associative thickening polymer capable of interacting with a hydrophobic phase and a hydrophilic phase; and wherein the associative thickening polymer comprises hydrophobic moieties and hydrophilic moieties; and wherein the formulation comprises at least 1.2% of associative thickening polymer; and wherein the formulation comprises from about 1% to about 12% of an oxidising agent.

DETAILED DESCRIPTION OF THE INVENTION

Figure 2:
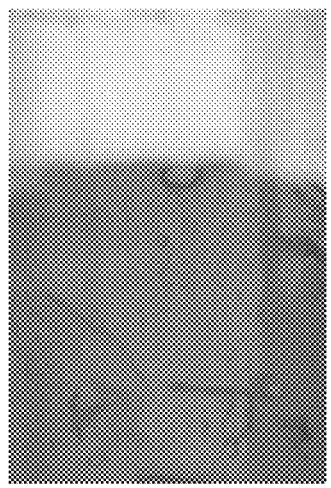
FIG. 2: Same as in FIG. 1, but after 30 min.
Figure 4:
FIG. 4: Same as in FIG. 3, but after 30 min.
Figure 1:
FIG. 1: Shows a qualitative colour migration experiment. The photograph displayed is after 1 min. The amount of migration between a first composition (left) according to the present invention (comprising a mixture of 10 parts colour formulation F, 10 parts developing formulation III, and 1 part thickening formulation 3 [refers to the tables in the example section below]) and a second composition (right) according to the present invention (comprising a mixture of 10 parts colour formulation C, 10 parts developing formulation III, and 1 part thickening formulation 3) is shown.
Figure 3:
FIG. 3: Shows a qualitative colour migration experiment after 1 min. The amount of migration between a first composition (left) according to the present invention (comprising a mixture of 10 parts colour formulation C, 10 parts developing formulation III, and 1 part thickening formulation 5) and a second composition (right) according to the present invention (comprising a mixture of 10 parts colour formulation F, 10 parts developing formulation III, and 1 part thickening formulation 5) is shown.
Figure 6:
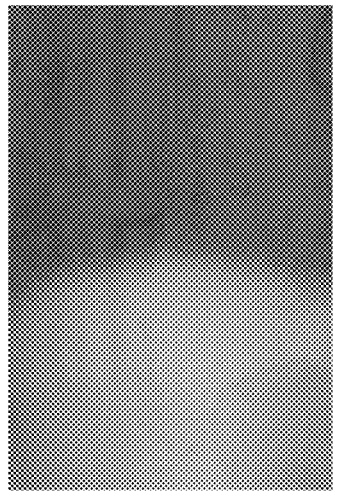
FIG. 6: Shows a qualitative colour migration experiment. The photograph displayed is after 30 min. The amount of migration between a first composition (left) according to the present invention (comprising a mixture of 10 parts colour formulation C, 10 parts developing formulation III, and 1 part thickening formulation 2) and a second composition (right) according to the present invention (comprising a mixture of 10 parts colour formulation A, 10 parts developing formulation III, and 1 part thickening formulation 2) is shown.
Figure 7:
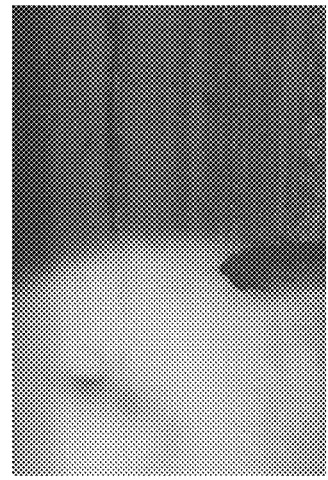
FIG. 7: Shows a qualitative colour migration experiment. The photograph displayed is after 30 min. The amount of migration between a first composition (left) according to the present invention (comprising a mixture of 10 parts colour formulation C, 10 parts developing formulation III, and 1 part thickening formulation 5) and a second composition (right) according to the present invention (comprising a mixture of 10 parts colour formulation A, 10 parts developing formulation III, and 1 part thickening formulation 5) is shown.
Figure 5:
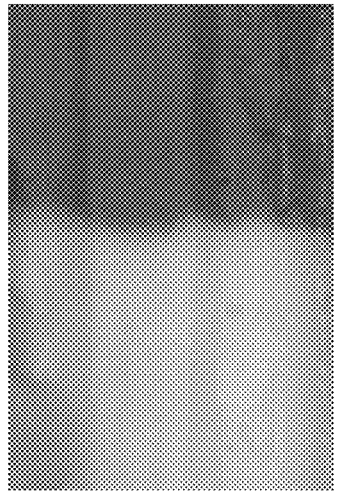
FIG. 5: Shows a qualitative colour migration experiment. The photograph displayed is after 30 min. The amount of migration between a first composition (left) according to the present invention (comprising a mixture of 10 parts colour formulation C, 10 parts developing formulation III, and 1 part thickening formulation 3) and a second composition (right) according to the present invention (comprising a mixture of 10 parts colour formulation A, 10 parts developing formulation III, and 1 part thickening formulation 3) is shown.
Figure 9:
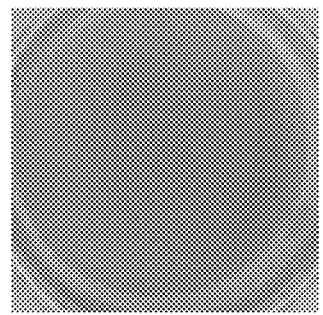
FIG. 9: Shows a qualitative colour migration experiment. The photograph displayed is the same as in FIG. 8, but after 30 min.
Figure 11:
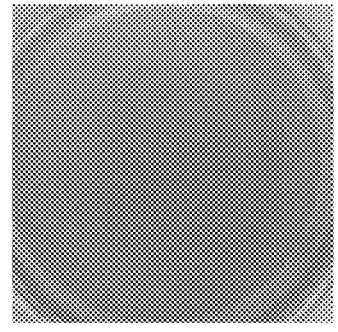
FIG. 11: Shows a qualitative colour migration experiment. The photograph displayed is the same as in FIG. 10, but after 30 min.
Figure 8:
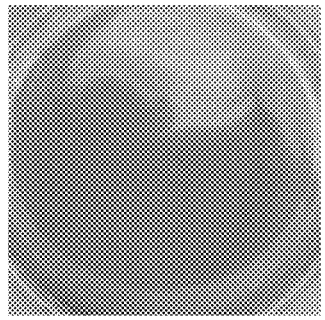
FIG. 8: Shows a qualitative colour migration experiment. The photograph displayed is after 1 min. The amount of migration between colour formulation H (left) and a water (right) is shown.
Figure 10:
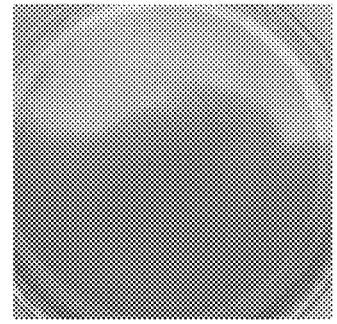
FIG. 10: Shows a qualitative colour migration experiment. The photograph displayed is after 1 min. The amount of migration between colour formulation H (left) and colour formulation I (right) is shown.
Figure 12:
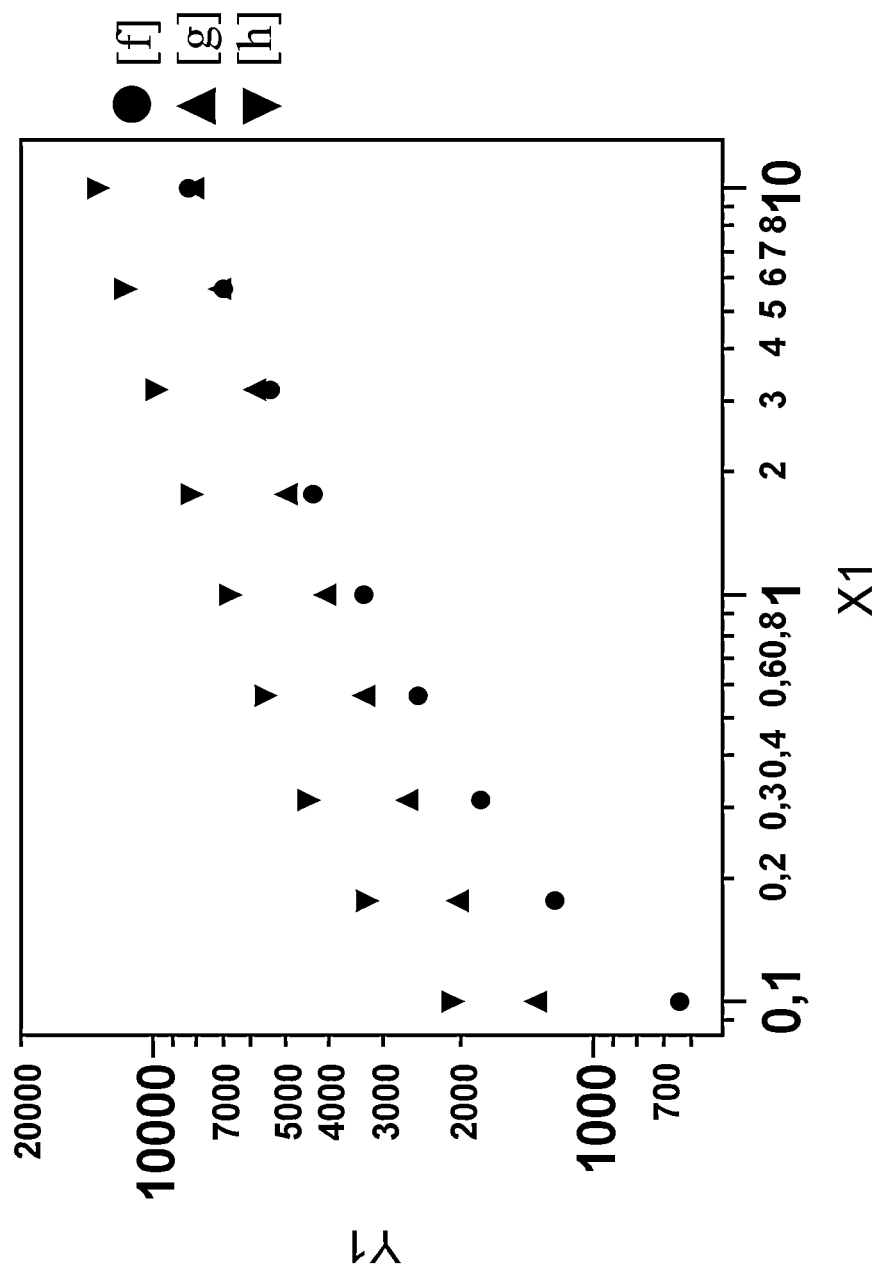
FIG. 12: Shows a rheology graph. X1=angular frequency [rad/s]. Y1=storage modulus, G' [Pa]. Compositions [f], [g] and [h] were tested—see "Experiment 1—Compositions tested" in the Data section below. Composition [f] is not pursuant to the present invention.
Figure 13:
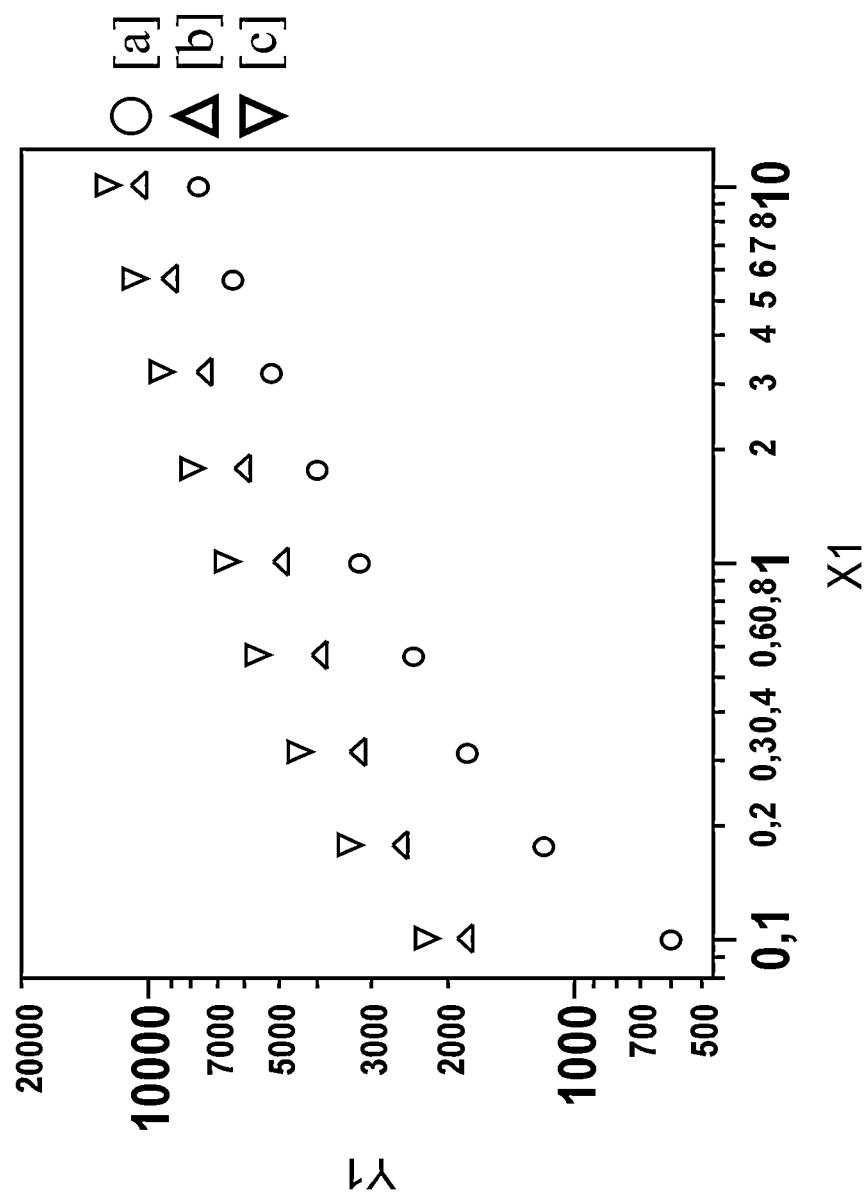
FIG. 13: Shows a rheology graph. X1=angular frequency [rad/s]. Y1=storage modulus, G' [Pa]. Compositions [a], [b] and [c] were tested—see "Experiment 1—Compositions tested" in the Data section below. Composition [a] is not pursuant to the present invention.
Figure 14:
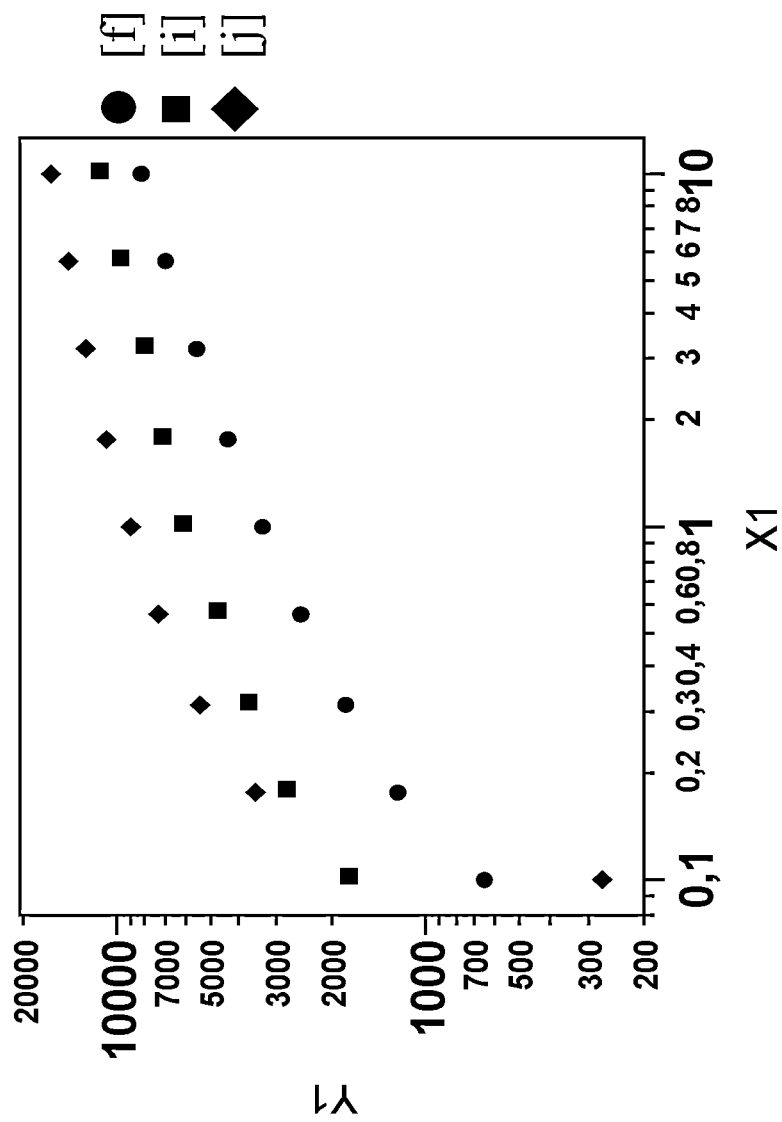
FIG. 14: Shows a rheology graph. X1=angular frequency [rad/s]. Y1=storage modulus, G' [Pa]. Compositions [f], [i] and [j] were tested—see "Experiment 1—Compositions tested" in the Data section below. Composition [f] is not pursuant to the present invention.
Figure 15:
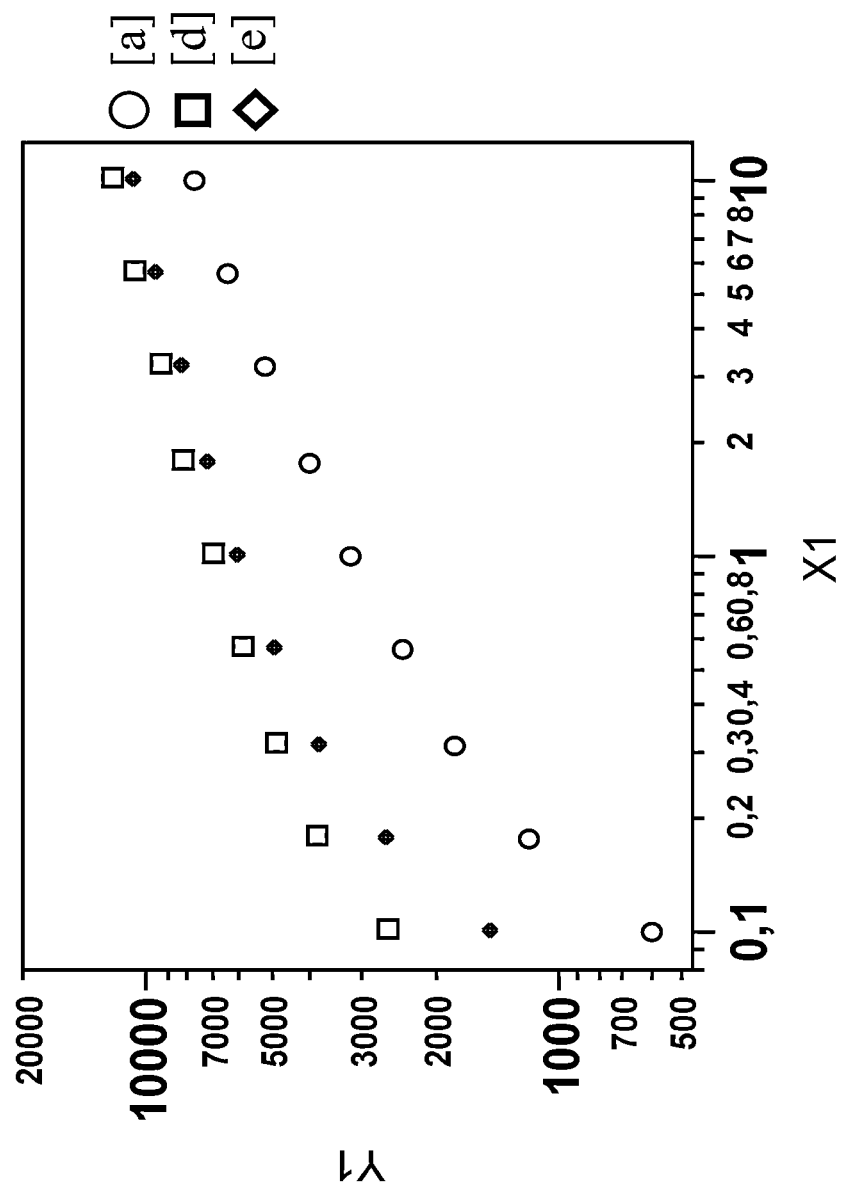
FIG. 15: Shows a rheology graph. X1=angular frequency [rad/s]. Y1=storage modulus, G' [Pa]. Compositions [a], [d] and [e] were tested—see "Experiment 1—Compositions tested" in the Data section below. Composition [a] is not pursuant to the present invention.
Figure 16:
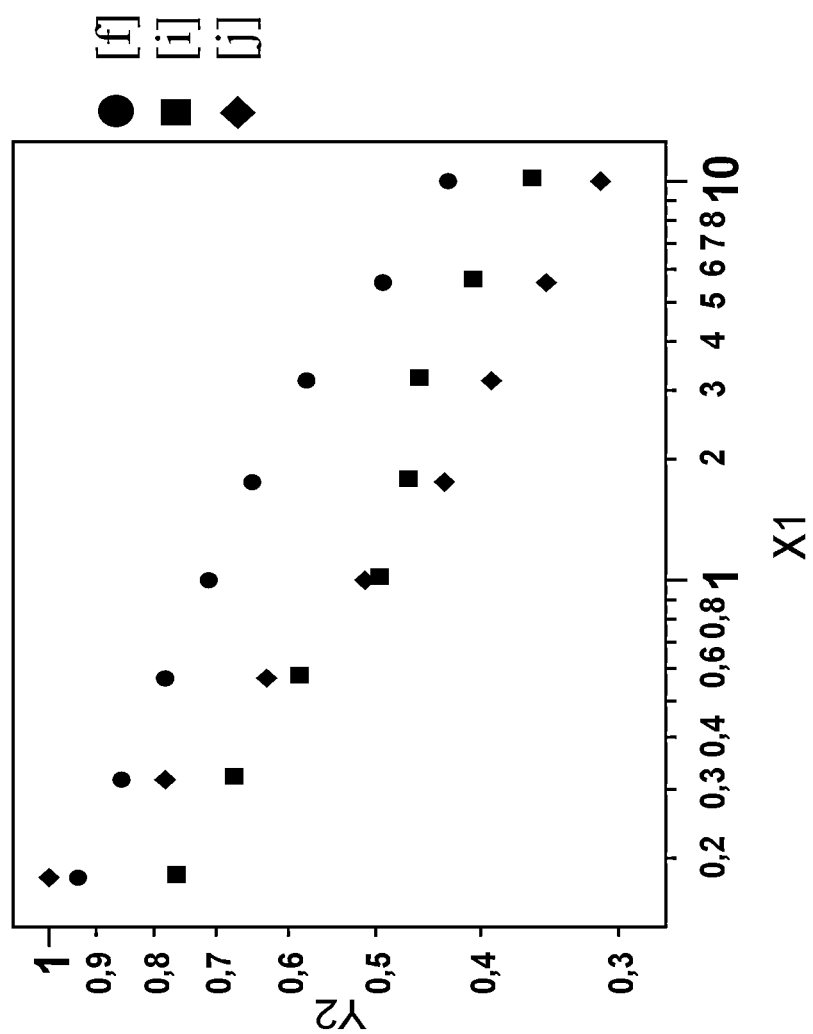
FIG. 16: Shows a rheology graph. X1=angular frequency [rad/s]. Y2=loss factor, tan δ. Compositions [f], [i] and [j] were tested—see "Experiment 1—Compositions tested" in the Data section below. Composition [f] is not pursuant to the present invention.
Figure 17:
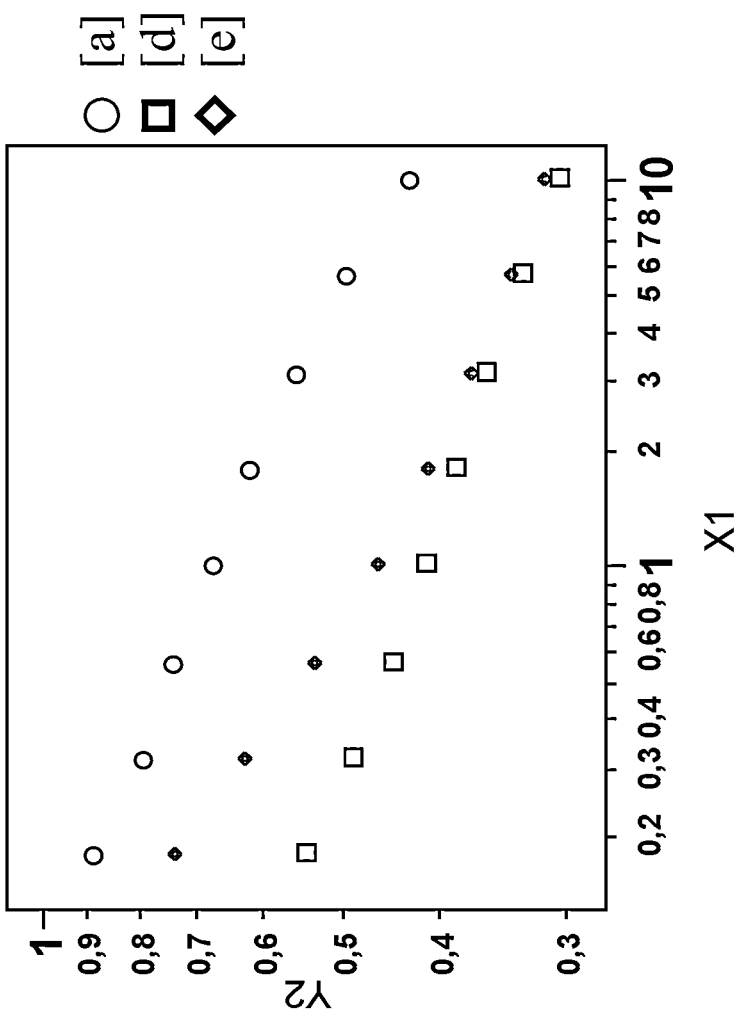
FIG. 17: Shows a rheology graph. X1=angular frequency [rad/s]. Y2=loss factor, tan δ. Compositions [a], [d] and [a] were tested—see "Experiment 1—Compositions tested" in the Data section below. Composition [a] is not pursuant to the present invention.
Figure 18:
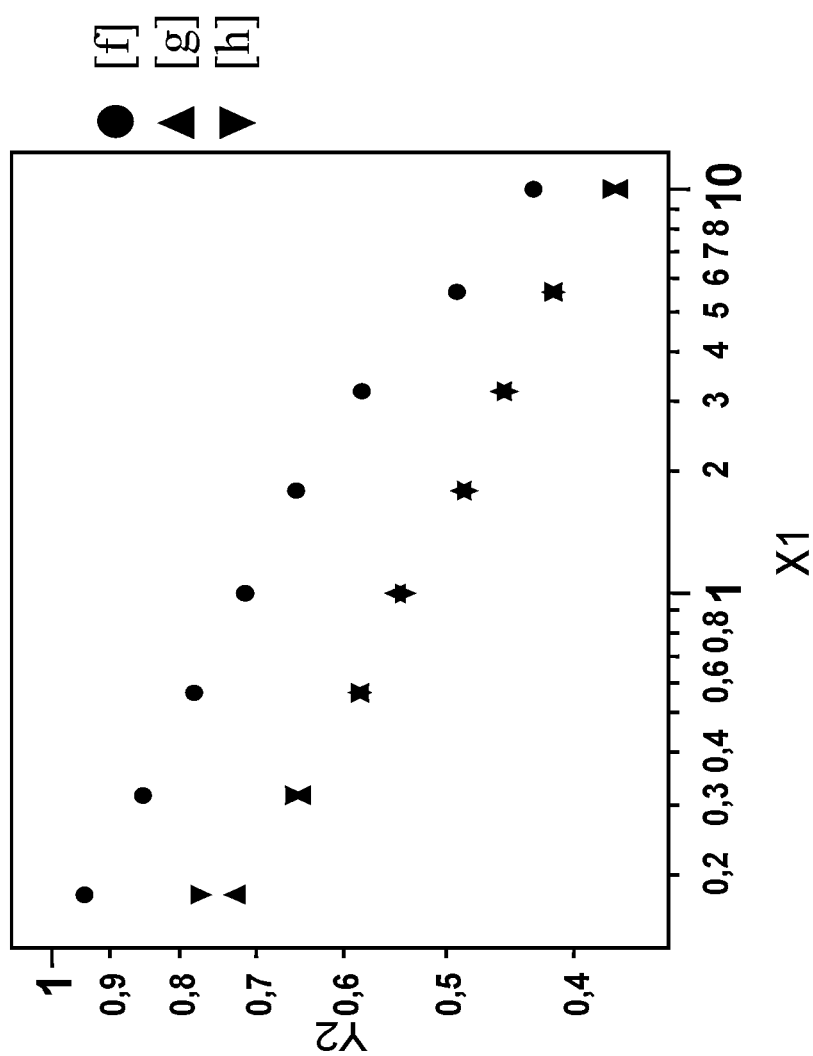
FIG. 18: Shows a rheology graph. X1=angular frequency [rad/s]. Y2=loss factor, tan δ. Compositions [f], [g] and [h] were tested—see "Experiment 1—Compositions tested" in the Data section below. Composition [f] is not pursuant to the present invention.
Figure 19:
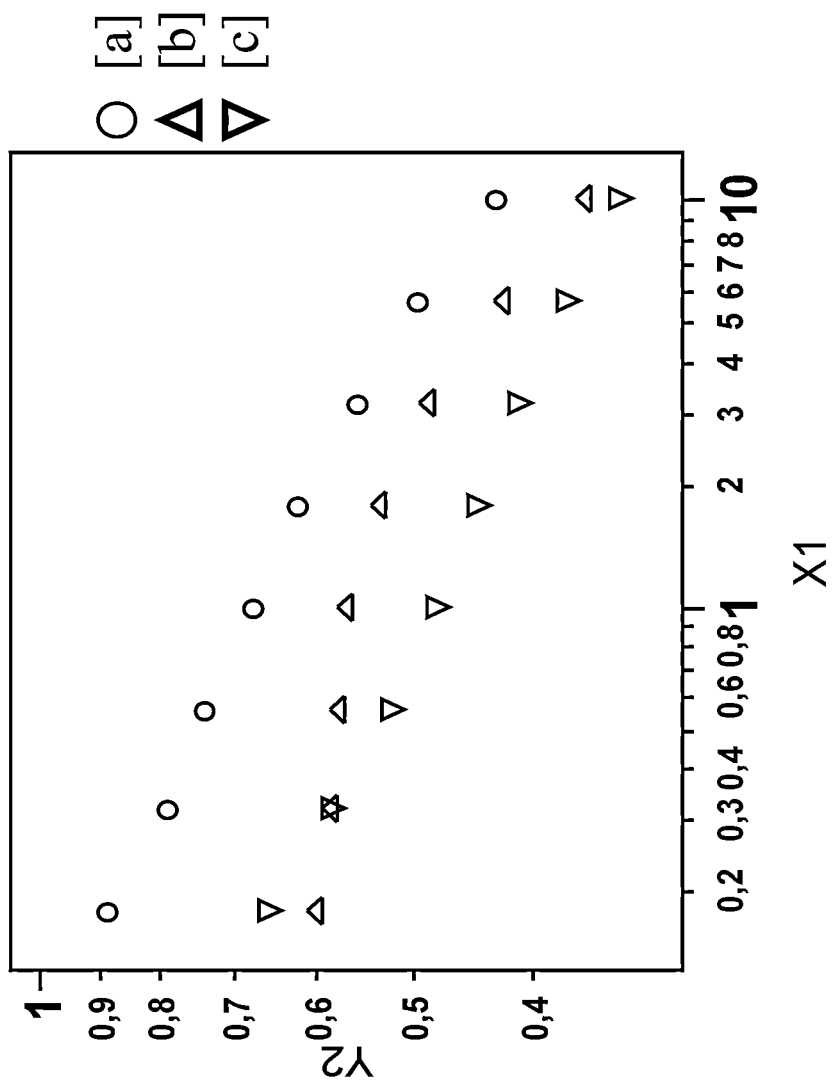
FIG. 19: Shows a rheology graph. X1=angular frequency [rad/s]. Y2=loss factor, tan δ. Compositions [a], [b] and [c] were tested—see "Experiment 1—Compositions tested" in the Data section below. Composition [a] is not pursuant to the present invention.

In all embodiments of the present invention, all percentages are by weight of the total composition, unless specifically stated otherwise. All ratios are weight ratios, unless specifically stated otherwise. References to 'parts' e.g. a mixture of 1 part X and 3 parts Y, is by weight unless stated otherwise. QSP means add a sufficient quantity for 100%. All ranges are inclusive and combinable. The number of significant digits conveys neither a limitation on the indicated amounts nor on the accuracy of the measurements.

All numerical amounts are understood to be modified by the word "about" unless otherwise specifically indicated. Unless otherwise indicated, all measurements are understood to be made at 23° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified. Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

The term "substantially free from" or "substantially free of" as used herein means less than about 1%, or less than 0.8%, or less than 0.5%, or less than 0.3%, or about 0%, by total weight of the composition or formulation.

"Hair", as used herein, means mammalian hair including scalp hair, facial hair and body hair, more preferably hair on the human head and scalp. "Hair shaft" or "hair fibre" means an individual hair strand and may be used interchangeably with the term "hair." "Proximal to the scalp," as used herein, means that portion of an extended, or substantially straightened, hair shaft that is closer in distance to the scalp than to the end of the hair. Thus, about 50% of the hair would be considered proximal to the scalp, and about 50% of the hair would be distal to the scalp. "z cm proximal to the scalp" means a distance "z" along the hair, with one endpoint being on or directly adjacent to the scalp, and the second endpoint being measured "z" centimetres along the length of the extended or substantially straightened hair.

"Cosmetically acceptable," as used herein, means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives," as used herein, includes but is not limited to, amide, ether, ester, amino, carboxyl, acetyl, acid and/or alcohol derivatives of a given compound.

"Monomer," as used herein, means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit", as used herein, means a monomer that has already been polymerised i.e. is part of the polymer.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be random, alternating or blockwise (i.e. block copolymer). Except if stated otherwise, the term "polymer" used herein includes any type of polymer including homopolymers and copolymers.

"Associative thickening polymers" are polymers that are based on water-soluble polymers. These can be acrylate polymers, cellulose ethers or, polyethyleneglycol. These typically comprise sidechains that are capped with water-insoluble hydrophobic groups like fatty alcohols, for example. In an aqueous solution or in emulsion, these polymers form a network that increases the viscosity of the solution/emulsion. The water-soluble backbone polymer is dissolves in water. The hydrophobic caps are adsorbed onto the hydrophobic emulsion polymer particles, or they form micelle structures with hydrophobes from other polymers. As each associative thickening polymer contains at least two hydrophobic caps, the result is a three-dimensional network within the emulsion. This increases the viscosity. Mainly the high- and mid-shear viscosity is affected. Therefore, it improves antispatter and brush drag more than all other thickeners.

The term "molecular weight" or "M. Wt." as used herein refers to the number average molecular weight unless otherwise stated. All percentages are calculated by weight unless otherwise stated.

"Kit" as used herein, means a package comprising a plurality of components. "Kit" may be referred to as "kit-of-parts". An example of a kit is, for example, a first composition and a separately packaged second composition and optionally application instructions.

"Implement," as used herein, means a device used to facilitate application of a composition to the hair and/or manipulation of the hair.

The inventors have answered the aforementioned needs by carefully selecting the specific combination of mutually compatible features such that the interaction therewith results in a method which provides the following benefits. Firstly, the method allows the stylist to design the colouring to the final hairstyle by creating the hairstyle during the application of the hair colouring agent. This ability is due to the sculptability and hold benefits afforded by the composition(s) as described herein. The stylist therefore has greater artistic freedom to envisage the final hairstyle and the hair colouring effects fitting optimally thereto. In addition, hold provided by the composition provides the stylist with security and self-confidence because the section of hair coloured can be put in a specific orientation or placed in a specific location and it remains in this orientation/location. The stylist is thus able to achieve a wide variety of complex hairstyles, which may or may not be related to the hairstyle result when the hair is dry and the salon visit is over. The method saves waste because the use of solid barrier means e.g. aluminium foils, is not necessary, since the hold/sculptability provided by the composition creates sufficient separation. The lack of foils also means that the stylist can better see where he or she is applying the colouring agent and where this is in relation to the entire head of hair. The method is also faster to execute than with foils. The method also provides an aesthetic improvement of the application process—a variety of hair styles can be created during the application of the hair colouring agent. Furthermore, the method is easier for apprentice/trainee stylists to learn—highlighting with foils requires excellent technique and significant practice—whereas the method according to the present invention is much faster to learn. Moreover, the method provides a way for consumers to create simple high- or low-lights at home since use of foils at home can be impractical and difficult to apply with one pair of hands.

The first composition comprises a first hair colouring agent, a hydrophobic phase, a hydrophilic phase, a surfactant, and a thickener capable of interacting with the hydrophobic phase and the hydrophilic phase. Without being bound by theory, it is believed that when the selected thickener is mixed with a hydrophobic phase in the context of this composition, the thickener interacts with the rheological structure of the hydrophobic phase resulting in altered visco-elastic properties of the resulting composition, in other words stiffer and more elastic composition. In particular, it is thought that the thickener interacts with a lamellar structure of the composition or micelles in the composition. These micelles or the lamellar structure exist due to the presence of both a of hydrophobic phase and hydrophilic phase in the composition. The stiffer and more elastic properties of the composition mean that the mobility of the composition is reduced—it is less able to flow and slide over itself, which provides hold and sculptability to hair fibres coated with the composition.

The method does not comprise the application of a solid barrier means in order to separate the first plurality of coated hair fibre portions from the second plurality of hair fibre portions. Without being bound by theory, it is believed that the altered stiffness and elastic properties reduces the miscibility of the hair colouring agent and also results in slower diffusion of the hair colouring agent. This means that a solid barrier means can be avoided since minimal or no staining occurs. "Staining" as used herein, means the unintentional dyeing of hair, typically due to unintended contact of the hair with a hair colouring agent. Staining may result from the transfer/migration of a colouring agent from one plurality of hair fibres to another plurality of hair fibres.

The features of the method according to the first aspect, as well as the other aspects and other relevant components, are described in detail hereinafter.

The method of the first aspect relates to a first composition comprising a first hair colouring agent a hydrophobic phase, a hydrophilic phase, a surfactant, and a thickener capable of interacting with the hydrophobic phase and the hydrophilic phase. In an embodiment, the method comprises a second composition, wherein the second composition comprises a second hair colouring agent, a hydrophobic phase, a hydrophilic phase, a surfactant, and a thickener capable of interacting with the hydrophobic phase and the hydrophilic phase. The method may also comprise a third and optionally fourth and optionally fifth composition, wherein the each composition comprises a third/fourth/fifth etc hair colouring agent, a hydrophobic phase, a hydrophilic phase, a surfactant, and a thickener capable of interacting with the hydrophobic phase and the hydrophilic phase. Where the phrase "the first composition and/or the second composition" is used, then the following also applies to said third, fourth and fifth composition.

The first composition comprises a hair colouring agent. The hair colouring agent may be selected from the group consisting of: direct dyes, oxidative dye compounds, and mixtures thereof. In an embodiment, the first and/or second composition is obtained by mixing together a colour formulation, a thickening formulation, and a developing formulation. In an embodiment, the first and/or second composition is obtained by mixing together a colour formulation and a developing formulation or a thickening formulation.

The first composition and/or the second composition may comprise a direct dye. In an embodiment, the hair colouring agent, for example the first hair colouring agent and/or the second hair colouring agent, is a direct dye. The direct dye may be present in an amount of from about 0.001% to about 4%, or from about 0.005% to about 3%, or from about 0.01% to about 2%, by total weight of the colour formulation or the composition. The presence of a direct dye and the proportion thereof is useful in that it can provide or enhance colouring/dyeing, particularly with regard to intensity. The direct dye may be selected from the group consisting of: nitro dyes to provide a blue colour, nitro dyes to provide a red colour, nitro dyes to provide a yellow colour, quinone dyes, basic dyes, neutral azo dyes, acid dyes, and mixtures thereof. In an embodiment, the direct dye is a nitro dye to provide a blue colour. In an embodiment, the direct dye is a nitro dye to provide a red colour. In an embodiment, the direct dye is a nitro dye to provide a yellow colour. In an embodiment, the direct dye is a quinone dye. In an embodiment, the direct dye is a basic dye. In an embodiment, the direct dye is a neutral azo dye. In an embodiment, the direct dye is an acid dye. In an embodiment, the direct dye is selected from the group consisting of: Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 16, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methyl-morpholin-4-ium-methylsulfate, (E)-1-(2-(4-(4,5-dimethyl-thiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl) butane-1-sulfonate, (E)-4-(4-(2-methyl-2-phenylhydrazono) methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide, Disperse Dyes such as Disperse Red 17, Disperse Violet 1, Disperse Red 15, Disperse Violet 1, Disperse Black 9, Disperse Blue 3, Disperse Blue 23, Disperse Blue 377, Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'42-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal.

The first composition and/or the second composition may comprise an oxidative dye compound. In an embodiment, the first and/or second composition comprise a hair colouring agent, wherein the hair colouring agent is an oxidative dye compound. In an embodiment, the first and/or second hair colouring agent are oxidative dye compounds; and wherein the first and/or second composition comprises an oxidising agent. The oxidative dye compound may be selected from the group consisting of: primary intermediates, couplers, and mixtures thereof. In an embodiment, the hair colouring agent is a mixture of at least one primary intermediate and at least one coupler. The oxidative dye compound may also be in the form of an oxidative stable direct dye. In an embodiment, the hair colouring agent is a mixture of at least one primary intermediate, at least one coupler and at least one oxidative stable direct dye. The oxidative dye compounds suitable for use in composition described herein, in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

Oxidative dye compounds are known in the art, and include aromatic diamines, aminophenols, aromatic diols and their derivatives (a representative but not exhaustive list of oxidation dye precursors can be found in Sagarin, "Cosmetic Science and Technology", "Interscience, Special Edn. Vol. 2 pages 308 to 310). It is to be understood that the primary intermediates and couplers (also collectively known as oxidative dye precursors) detailed below are only by way of example and are not intended to limit the compositions and processes herein. The primary intermediates and couplers may be used in the form of salts.

In an embodiment, the primary intermediate is selected from the group consisting of: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino) phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, and mixtures thereof. In an embodiment, the primary intermediate is 2-methoxymethyl-1,4-benzenediamine, which may be preferred due to improved sensitisation profile. This may be preferred for the present invention due to the method comprising a styling step.

In an embodiment, the coupler is selected from the group consisting of: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene) bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The primary intermediates and couplers may be present in an amount of from about 0.001% to about 12%, or from about 0.01% to about 10%, or from about 0.05% to about 9%, or from about 1% to about 6%, by total weight of the composition or colour formulation. In an embodiment, the compositions and/or formulation is substantially free of a direct dye.

In an embodiment, the first and/or second composition comprises an oxidizing agent. The oxidizing agent may be present in an amount sufficient to bleach melanin pigment in hair and/or cause formation of dye chromophores from oxidative dye compounds (including primary intermediates and/or couplers, when present). In an embodiment, the thickening formulation and/or the developing formulation comprise an oxidising agent. In an embodiment, the oxidising agent is present in an amount of from about 0.1% to about 20%, or from about 0.5% to about 12%, or from about 1% to about 10%, or from about 3% to about 10%, or from about 5% to about 10% by total weight of the thickening formulation or the developing formulation. In an embodiment, the oxidising agent is present in an amount of from about 0.1% to about 20%, or from about 1% to about 10%, or from about 2% to about 5%, by total weight of the first composition or the second composition. Inorganic peroxygen materials capable of yielding hydrogen peroxide in an aqueous medium may be used. In an embodiment, the oxidising agent is selected from group consisting of: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, particularly sodium salts thereof), which may be incorporated as monohydrates, tetrahydrates, etc.; alkali metal bromates; enzymes; and mixtures thereof. In an embodiment, the oxidizing agent is a percarbonate (such as sodium percarbonate, ammonium percarbonate and potassium percarbonate). In another embodiment, the oxidizing agent is sodium percarbonate. In an embodiment, the first composition and/or second composition is substantially free of persulfate. In an embodiment, all compositions and formulations are substantially free of persulfate. In an embodiment, the method does not encompass or include bleaching the hair.

A composition and/or formulation as described herein may comprise at least one source of peroxymonocarbonate ions, e.g. formed in situ from a source of hydrogen peroxide and a carbonate ion source. The composition/formulation thus also may comprise a source of carbonate ions or carbamate ions or hydrocarbonate ions or any mixture thereof. The source may be selected from the group consisting of: sodium, potassium, guanidine, arginine, lithium, calcium, magnesium, barium, ammonium salts of carbonate, carbamate and hydrocarbonate ions, and mixtures thereof. Examples of mixtures thereof are: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate, and mixtures thereof. Percarbonate salts may also be utilized to provide both the source of carbonate ions and oxidizing agent. The source of carbonate ions, carbamate and hydrocarbonate ions may be selected from the group consisting of: sodium hydrogen carbonate, potassium hydrogen carbonate, ammonium carbamate, and mixtures thereof.

A composition and/or formulation as described herein may comprise a radical scavenger, in a sufficient amount to reduce damage to the hair during an oxidative bleaching or colouring process. The radical scavenger is preferably selected such that it is not an identical species to an alkalising agent. The radical scavenger is a species that can react with a carbonate radical to convert the carbonate radical by a series of fast reactions to a less reactive species. The radical scavenger may be selected from the classes of: alkanolamines, amino sugars, amino acids, and mixtures thereof. The radical scavenger may be selected from the group consisting of: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan, and potassium, sodium and ammonium salts of the above, and mixtures thereof. In an embodiment, the radical scavenger compound is selected from the group consisting of: benzylamine, glutamic acid, imidazole, di-tert-butylhydroxytoluene, hydroquinone, catechol, and mixtures thereof.

A composition and/or formulation as described herein may comprise a chelant in an amount sufficient to reduce the amount of metals available to interact with formulation components, e.g. oxidizing agents, more particularly peroxides. Chelants are also known as chelators. The chelant for use herein may be selected from the group consisting of: diamine-N,N'-dipolyacid, monoamine monoamide-N,N'-dipolyacid, and N,N'-bis(2-hydroxybenzyl)ethylenediamine-N,N'-diacetic acid chelants (e.g. EDDS (ethylenediaminedisuccinic acid)), carboxylic acids (e.g. aminocarboxylic acids), phosphonic acids (e.g. aminophosphonic acids), polyphosphoric acids (in particular straight polyphosphoric acids), salts and derivatives thereof, and mixtures thereof. In an embodiment, the chelant is ethylenediamine tetraacetic acid (EDTA) and/or editronic acid.

The first composition comprises a thickener capable of interacting with the hydrophobic phase and the hydrophilic phase. In an embodiment, the second composition comprises a thickener capable of interacting with the hydrophobic phase and the hydrophilic phase. The first composition and/or the second composition may comprise from about 0.001% to about 10.0%, or from about 0.01%, or 0.05%, or 0.1%, or 0.15%, or 0.25%, or 0.6%, or 1%, or 2%, or 2.5% to about 8%, or 7%, or 6%, or 5%, or 4%, or 3%, or 2%, or 1%, of a thickener capable of interacting with the hydrophobic phase and the hydrophilic phase, by total weight of the first or second composition. In an embodiment, the first and/or second composition comprises from about 0.6% to about 8% associative thickening polymer. In an embodiment, the thickener is an associative thickening polymer comprising a hydrophilic backbone substituted with at least one hydrophobic sidechain, and wherein the composition comprises from about 0.6%, or 1%, or 2%, or 2.5% to about 8%, or 7%, or 6%, or 5%, or 4%, or 3%, or 2%, or 1%, of the associative thickening polymer.

In an embodiment, the thickener is an associative thickening polymer. In an embodiment, the thickener capable of interacting with the hydrophilic phase and capable of undergoing hydrophobic-hydrophobic interactions. In an embodiment, the thickener is an associative thickening polymer and comprises hydrophobic moieties and hydrophilic moieties. In an embodiment, the associative thickening polymer is a non-ionic or anionic polymer. The hydrophobic and hydrophilic moieties are important since they help the thickener interact with the hydrophobic phase and the hydrophilic phase. In an embodiment, the hydrophobic moieties of the associative thickening polymer are is capable of interacting with themselves and with the hydrophobic phase of the first and/or second composition. In an embodiment, associative thickening polymer is a block copolymer comprising hydrophobic blocks and hydrophilic blocks. In an embodiment, the block copolymer is an ABA-triblock copolymer. In an embodiment, the block copolymer is a polyurethane copolymer. In an embodiment, the hydrophilic blocks of the block copolymer comprise fatty alcohols. In an embodiment, associative thickening polymer comprises hydrophobic moieties on the end of sidechains. In an embodiment, the hydrophobic moieties and/or hydrophobic blocks of the thickener consist of carbon and hydrogen atoms. In an embodiment, the associative thickening polymer comprises hydrophobic moieties and these comprise a saturated hydrocarbon chain consisting of carbon and hydrogen atoms. The associative thickening polymer may comprise a hydrophilic backbone substituted with at least one hydrophobic sidechain. The hydrophobic sidechain is important since it aids the associative thickening polymer to interact with the hydrophobic phase. In an embodiment, the associative thickening polymer comprises a unit comprising an acrylate group and a sidechain capable of forming hydrophobic interactions, particularly a sidechain comprising a saturated hydrocarbon chain consisting of carbon and hydrogen atoms. In an embodiment, the acrylate group is derived from the polymerisation of vinyl groups. In an embodiment, the backbone comprises acrylate, itaconate and/or urethane groups. In an embodiment, the hydrophilic moieties comprise urethane units. In an embodiment, the associative thickening polymer is substituted with a hydrophobic sidechain comprising at least 10 carbon atoms, or from 12 to 24 carbon atoms. The hydrophobic sidechain may comprise at least about 8 carbon atoms, or at least about 10 carbon atoms, or from about 10 to about 30 carbon atoms, or from about 15 to about 25 carbon atoms, or from about 18 to about 20 carbon atoms. In an embodiment, the associative thickening polymer is crosslinked, for example via inter-strand crosslinks. In an embodiment, the thickener is selected from the group consisting of: Acrylates/Ceteth-20 Itaconate Copolymers, Polyurethane-39 polymers, Acrylates/Beheneth-25 Methacrylate Copolymers, Acrylates/C10-30 Alkyl Acrylate Crosspolymers, Sodium Acrylate/Sodium Acryloyldimethyl Taurate Copolymers, and mixtures thereof. In an embodiment, the associative thickening polymer is selected from the group consisting of: Acrylates/Ceteth-20 Itaconate Copolymers, Polyurethane-39 polymers, Acrylates/Beheneth-25 Methacrylate Copolymers, Acrylates/C10-30 Alkyl Acrylate Crosspolymers, Acrylates/C10-30 Alkylacrylates Copolymers and mixtures thereof. In an embodiment, the associative thickening polymer is selected from the group consisting of: an Acrylates/Ceteth-20 Itaconate copolymer, a polyurethane polymer (e.g. Polyurethane-39), an Acrylates/Beheneth-25 Methacrylate Copolymer, and mixtures thereof. In an embodiment, the polyurethane polymer is a Polyurethane-39 polymer. In an embodiment, the thickener or associative thickening polymer is not a Sodium Acrylate/Sodium Acryloyldimethyl Taurate Copolymer. Indeed, Sodium Acrylate/Sodium Acryloyldimethyl Taurate Copolymer does not comprise moieties within the polymer itself that are capable of interacting with the hydrophobic phase. In an embodiment, the associative thickening polymer is an Acrylates/Ceteth-20 Itaconate Copolymer. In an embodiment, the associative thickening polymer is not an Acrylates/Ceteth-20 Itaconate Copolymer. Suitable thickeners may include: Luvigel® Star from BASF, Structure® 3001 from Akzo Nobel, Structure® 2001 from Akzo Nobel, Aculyn™ 28 from Dow Personal Care, Pemulen™ TR1 from Lubrizol, Pemulen™ TR2 from Lubrizol, Carbopol® Ultrez 20 from Lubrizol, Carbopol® Ultrez 21 from Lubrizol, Carbopol® Ultrez 10 from Lubrizol, ViscUp® EZ from Arch Chemicals, and mixtures thereof.

In an embodiment, the first composition and/or the second composition has a storage modulus of at least about 3000 Pa, or at least about 3300 Pa, or at least about 3500 Pa, or at least about 4000 Pa, or at least about 4500 Pa, or at least about 5000 Pa, measured by frequency sweep at an angular frequency of 0.6 rad/s at 23° C. In an embodiment, the first and/or second composition has a storage modulus of at least about 3000 Pa, or at least about 3300 Pa, or at least about 3500 Pa, or at least about 4000 Pa, or at least about 4500 Pa, or at least about 5000 Pa, measured by frequency sweep at an angular frequency of 0.6 rad/s at 23° C.; and wherein the thickener is an associative thickening polymer and comprises hydrophobic moieties and hydrophilic moieties; and wherein the first and/or second composition comprises from about 0.6% to about 8% associative thickening polymer.

The first composition comprises a hydrophobic phase. In an embodiment, the second composition comprises a hydrophobic phase. In an embodiment, the hydrophobic phase comprises: fatty alcohols, fatty acids, or mixtures thereof. In an embodiment, the fatty alcohols and/or fatty acids comprise from 10 to 30, or from 12 to 20, or from 16 to 18 carbon atoms. In an embodiment, the colour formulation comprises a hydrophobic phase. In an embodiment, the hydrophobic phase comprises two different fatty alcohols. In an embodiment, the hydrophobic phase comprises two different fatty alcohols, both comprising from about 10 to about 14 carbons.

The first composition comprises a hydrophilic phase. In an embodiment, the second composition comprises a hydrophilic phase. The hydrophilic phase may be in the form of a cosmetically acceptable carrier, for example an aqueous cosmetically acceptable carrier. A composition and/or formulation as described herein may comprise a cosmetically acceptable carrier. The composition/formulation may comprise from about 60% to about 99.9%, or from about 70% to about 95%, or from about 80% to about 90%, of a cosmetically acceptable carrier, by total weight of the composition or formulation. The cosmetically acceptable carrier may comprise water; silicones such as volatile silicones, amino or non-amino silicone gums; organic compounds such as $C_2$-$C_{10}$ alkanes, acetone, methyl ethyl ketone, volatile organic $C_1$-$C_{12}$ alcohols, esters of $C_1$-$C_{20}$ acids and of $C_1$-$C_8$ alcohols such as methyl acetate, butyl acetate, ethyl acetate, and isopropyl myristate, dimethoxyethane, diethoxyethane, $C_{10}$-$C_{30}$ fatty alcohols such as lauryl alcohol, cetyl alcohol, stearyl alcohol, and behenyl alcohol; $C_{10}$-$C_{30}$ fatty acids such as lauric acid and stearic acid; $C_{10}$-$C_{30}$ fatty amides such as lauric diethanolamide; $C_{10}$-$C_{30}$ fatty alkyl esters such as $C_{10}$-$C_{30}$ fatty alkyl benzoates; hydroxypropylcellulose, and mixtures thereof. In an embodiment, the carrier comprises water, fatty alcohols, volatile organic alcohols, and mixtures thereof. In an embodiment, the cosmetically acceptable carrier is water.

A composition and/or formulation as described herein may comprise a pH modifier and/or buffering agent in an amount that is sufficiently effective to adjust the pH of the composition/formulation to fall within a range from about 3 to about 13, or from about 7 to about 12, or to about 11, or to about 10, or to about 9, or to about 8. In an embodiment, the first composition and/or second composition has a pH of about 7 to about 9. In some embodiments, the pH range for the carbonate ion source as described herein below is from about 8.5 to about 9.5, or from about 8.0 to about 9.0. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3-propandiol and guanidium salts, alkali metal and ammonium hydroxides and carbonates, preferably sodium hydroxide, sodium silicate, sodium meta silicate and ammonium carbonate, and acidulents such as inorganic and inorganic acids, e.g., phosphoric acid, acetic acid, ascorbic acid, citric acid or tartaric acid, hydrochloric acid, and mixtures thereof.

A composition and/or formulation as described herein may comprise an alkalising agent. By "alkalising agent" it is meant one or more compound suitable for raising the pH to alkaline level, in particular to a pH between 9 and 11. Generally, the most commonly used alkalising agent in the art is ammonia. Non-ammonia alkalising agents are also known and preferred due to reduced olfactory stimulation. For example, alkanolamines such as monoethanolamine. A composition and/or formulation as described herein may comprise a non-ammonia alkalising agent selected from the group consisting of: monoethanolamine (MEA), sodium silicate, sodium meta silicate, diethanolamine, triethanolamine, monopropanolamine, dipropanolamine, tripropanolamine, 2-amino-2-methyl-1,3-propanediol, 2-amino-2-methyl-1-propanol (a.k.a. aminomethylpropanol, AMP), 2-amino-2-hydroxymethyl-1,3-propanediol, and mixtures thereof. Monoethanolamine (MEA) or aminomethylpropanol (AMP) are commonly used in ammonia-free hair dye products and may be preferred as the alkalising agent alone or in combination with each other or other alkalising agents. Monoethanolamine may be in particular be preferred to be used alone or in combination with other non-ammonia alkalising agent. A composition and/or formulation as described herein may comprise ammonia in addition to the non-ammonia alkalising agent, for example less than 0.5% ammonia. In an embodiment, the alkalising agent is monoethanolamine (MEA). In an embodiment, the first and/or second composition comprises the alkalising agent monoethanolamine (MEA) and the oxidative dye compound is 2-methoxymethyl-1,4-benzenediamine.

In an embodiment, the first composition and/or the second composition comprises a surfactant. The first composition and/or the second composition may comprise from about 0.001% to about 10%, or from about 0.1% to about 8%, or from about 0.5% to about 5%, or from about 0.4% to about 2%, or from about 0.8% to about 1.5%, of a surfactant, by total weight of the first composition or the second composition. The surfactant may be selected from the group consisting of: anionic surfactants, amphoteric surfactants, a zwitterionic surfactants, a cationic surfactants, a non-ionic surfactants, or mixtures thereof. The surfactant is useful for stabilising the hydrophobic phase in the composition, for example stabilising the gel network and/or lamellar structure. In an embodiment, the anionic co-surfactant is sodium lauryl sulfate or sodium laureth sulfate. In an embodiment, the surfactant is a non-ionic surfactant. The non-ionic surfactant may be selected from the group consisting of lanolin alcohol, and polyoxyethylene ethers of fatty alcohols, and mixtures thereof. In an embodiment, the non-ionic surfactant is ceteareth-n, wherein n is from about 2 to about 100, or from about 10 to about 30.

In an embodiment, the first composition and/or the second composition is substantially free of: components capable of forming a neutral complex with the thickener, and/or a cationic polymer, and/or cationic surfactant.

The first composition and/or the second composition may be in the form of a cream or an emulsion. In an embodiment, first composition and/or the second composition has a lamellar structure and/or has a gel network. In an embodiment, first composition and/or the second composition comprises micelles comprising the hydrophobic phase.

In an embodiment, the "hair fibre portions" are those of doll heads or maniquin heads. In an embodiment, the "hair fibre portions" are those of synthetic hair. In an embodiment, the "hair fibre portions" are from keratin fibres.

In an embodiment, the first and/or second composition is obtained from mixing together a colour formulation, a thickening formulation, and a developing formulation. Said colour formulation, thickening formulation, and developing formulation may be as described herein. In an embodiment, the colour formulation comprises a hair colouring agent, a hydrophobic phase, a hydrophilic phase, and the developing formulation comprises an oxidising agent, and the thickening formulation comprises an associative thickening polymer capable of interacting with the hydrophobic phase and the hydrophilic phase and wherein the associative thickening polymer comprises a hydrophilic backbone comprising acrylates groups. In an embodiment, the thickening formulation comprises an oxidising agent and an associative thickening polymer capable of interacting with the hydrophobic phase and the hydrophilic phase and wherein the associative thickening polymer comprises a hydrophilic backbone comprising acrylates groups.

In an embodiment, the first and/or second composition is obtained from mixing together, at a certain ratio, a colour formulation, a developing formulation, and a thickening formulation. In an embodiment, the weight ratio of the colour formulation to the developing formulation (i.e. colour formulation:developing formulation) is from about 1:5 to about 5:1. If the colour formulation is part of a three-component mixture, this weight ratio is also valid. In an embodiment, the weight ratio of the colour formulation to the developing formulation to the thickening formulation (i.e. colour formulation:developing formulation:thickening formulation) is from about 10:10:0.5 to about 10:10:2, or from about 10:20:0.5 to about 10:20:2. In an embodiment, wherein the thickening formulation comprises an oxidising agent such as hydrogen peroxide, the first and/or second composition is obtained from mixing together, at a certain ratio, a colour formulation, and a thickening formulation. In this embodiment, the weight ratio of the colour formulation to the thickening formulation (i.e. colour formulation:thickening formulation) is from about 10:5 to about 10:25, or from about 10:8 to about 10:22, or from about 10:15 to about 10:20, or from about 10:8 to about 10:12, or from about 10:12 to about 10:18.

The method relates to the formation of a first plurality of coated hair fibre portions. As used herein, a "hair fibre portion" may be an entire fibre of hair from root to tip, alternatively it may relate only to a section of this fibre e.g. only the root section, or only the tip section. A "plurality of hair fibre portions" as used herein, relates to two or more hair fibre portions. Typically a plurality of hair fibre portions relates to a bundle of hair fibre portions, which have been gathered together such they are in close proximity i.e. in a bundle. The respective roots from which the bundle originates may also be in close proximity. For longer hair, however, this may not be the case. A plurality of hair fibre portions may relate to, for example, a bundle of circa 10 entire hair fibres from root to tip. Alternatively, a plurality of hair fibre portions may relate to a bundle of root portions of circa 50 hair fibres. The alternatives in the above description are due to variations in the colouring effects needed in order to create a specific hairstyle. For example, the target final hair effect may require a first hair colouring agent to be applied to circa 50% of the root portions, a second hair colouring agent to be applied to the remaining 50% of the root portions, and a third colouring agent to be applied to all of the tip portions. The term "coated hair fibre portion" as used herein means a section of a hair fibre that has been covered or coated, preferably over the majority of its surface area, with a composition. In an embodiment, the phrase "coated hair fibre portions, wherein the coating comprises a composition," means "hair fibre portions coated with a composition". The method comprises the formation of a first plurality of coated hair fibre portions, and subsequently styling the hair, wherein the first plurality of coated hair fibre portions is contacted with a second plurality of hair fibre portions. "Contacted with", as used herein, means placing two elements in close proximity such that they touch each other. When, the first plurality of coated hair fibre portions is contacted with a second plurality of hair fibre portions, only parts of the coating on the first plurality of coated hair fibre portions may touch the second plurality of hair fibre portions.

In an embodiment, the first plurality of coated hair fibre portions is formed by applying the first composition to a first plurality of hair fibre portions. In this embodiment, the first composition, comprising a first hair colouring agent and an associative thickening polymer (see above description), may be provided, and subsequently applied to the first plurality of hair fibre portions, thus forming the first plurality of coated hair fibre portions.

In another embodiment, the first plurality of coated hair fibre portions is formed by applying a first hair colouring agent to a first plurality of hair fibre portions and subsequently applying an associative thickening polymer to the (same) first plurality of hair fibre portions. This embodiment may be referred to as layering. In another form of layering, the first plurality of coated hair fibre portions is formed by applying an associative thickening polymer to a first plurality of hair fibre portions and subsequently applying a first hair colouring agent to the first plurality of hair fibre portions.

In an embodiment, the method further comprises:
the formation of a second plurality of coated hair fibre portions, wherein the coating comprises a second composition, wherein the second composition comprises a second hair colouring agent, a hydrophobic phase, a hydrophilic phase, a surfactant, and a thickener capable of interacting with the hydrophobic phase and the hydrophilic phase; and subsequently
contacting the first plurality of coated hair fibre portions with the second plurality of coated hair fibre portions.

The second hair colouring agent is different from the first hair colouring agent, which means the first hair colouring agent exhibits a different colour versus the colour exhibited by the second hair colouring agent. In an embodiment, the second plurality of coated hair fibre portions is formed by applying a second composition to a second plurality of hair fibre portions. The second plurality of coated hair fibre portions may alternatively be formed by 'layering' as described herein.

In an embodiment, the first plurality of hair fibre portions and the second plurality of hair fibre portions do not originate from substantially the same plurality of hair fibre roots.

In an alternative embodiment, the first plurality of hair fibre portions and the second plurality of hair fibre portions originate from substantially the same plurality of hair fibre roots. For example, the same plurality of hair fibre portions may be coated with both the first composition and the second composition. This may mean that the same plurality of hair fibre portions is dyed with different colours. For example the first plurality of hair fibre portions could be the root portion of the plurality of hair fibres, and this root portion could be coated with the first composition comprising the first hair colouring agent and an associative thickening polymer, and the second plurality of hair fibre portions could be the remaining portion of the plurality of hair fibres including the tip portion, and this remaining portion could be coated with the second composition comprising the second hair colouring agent and an associative thickening polymer.

In an embodiment, the first plurality of coated hair fibre portions is formed by applying the first composition to a first plurality of hair fibre portions, and subsequently applying a second composition to the first plurality of coated hair fibre portions, wherein the second composition comprises a second hair colouring agent and an associative thickening polymer. In this embodiment, substantially the same plurality of coated hair fibre portions is coated with both the first composition and the second composition. In this embodiment, the first composition and the second composition may be blended together on the hair fibre portions.

In an embodiment, a first, a second, a third and a fourth plurality of coated hair fibre portions are formed, wherein the coating comprises a composition comprising a hair colouring agent, a hydrophobic phase, a hydrophilic phase, a surfactant, and a thickener capable of interacting with the hydrophobic phase and the hydrophilic phase. In an embodiment, the composition for each coating comprises two or more different hair colouring agents, wherein the hair colouring agents may result in a different final colour result.

In an embodiment, the plurality of coated hair fibre portions are laid flat onto the head. In an embodiment, the plurality of coated hair fibre portions are in slice-shaped form. In an embodiment, the first plurality of coated hair fibre portions is sculpted to form a curl.

"Substantially the same", as used herein, means at least 50% the same, or more than 60% the same, or more than 70% the same, or more than 80% the same, or more than 90% the same, or more than 95% the same.

In an embodiment, the method results in a hairstyle and wherein the hairstyle is selected from the group consisting of: turban; plait; braid; tousel; wave; criss-cross; blending; 2-step; sculpting; and combinations thereof.

In an embodiment, prior to the formation of the second plurality of coated hair fibre portions, first plurality of hair fibre portions is styled to form a hairstyle. In an embodiment, subsequent to the formation of the second plurality of coated hair fibre portions, the second plurality of coated hair fibre portions is styled to form a hairstyle.

In an embodiment, the first hair colouring agent (and second hair colouring agent, when applied) is allowed to remain on the hair for a development time. The development time may be from about 1 min to about 90 min, or from about 5 min to about 70 min, or from about 10 min to about 60 min, or from about 10 min to about 40 min.

In an embodiment, prior to the formation of the second plurality of coated hair fibre portions, the hair is treated with a treatment. The treatment may selected from the group consisting of the exposure of the hair: to a temperature of 20° C. to 45° C., or 30° C. to 42° C. for at least 0.5 min, or at least 1 min, or at least 3 min, or at least 5 min; to a relative humidity of 20% to 80%, or 40% to 70% for at least 0.5 min, or at least 1 min, or at least 3 min, or at least 5 min; and combinations thereof.

In an embodiment of the method, after application of the first composition and, when applied, after application of the second composition, the composition(s) are subsequently rinsed from the hair.

Following hair rinsing, the hair displays a hair colour effect. The hair colour effect may be selected from the group consisting of: hair strand effects, highlighting, lowlighting, and combinations thereof.

The method does not comprise the application of a solid barrier means in order to separate the first plurality of coated hair fibre portions from the second plurality of hair fibre portions. "Solid barrier means", as used herein, means that a solid substance is placed on the hair, such that portions of the hair are not able to touch each other and thus no staining is possible. Foils are an example of solid barrier means, which are typically used such that portions of hair are individually wrapped in foil. Another example of a solid barrier means is a cap comprising holes. Such a cap is described, in particular in FIG. 2 and in § 0004 on p. 2, in European patent application EP1969961A2, filed on 10 Mar. 2008 in the name of the Procter & Gamble Co. and published on 17 Sep. 2008.

In an embodiment, the solid barrier means is a physical barrier selected from the group consisting of foil, plastic, film, cotton wool, padding material, caps, and combinations thereof.

In an embodiment, the method comprises the application of a liquid barrier means in order to separate the first plurality of coated hair fibre portions from the second plurality of hair fibre portions and such that no staining occurs. The liquid barrier means may be a conditioning formulation.

In another embodiment, method does not comprise the application of any barrier means in order to separate the first plurality of coated hair fibre portions from the second plurality of hair fibre portions. "Any barrier means" comprises liquid barrier means and solid barrier means.

An embodiment of the first aspect relates to a method for colouring hair, wherein the method comprises:
 (i) the formation of a first plurality of coated hair fibre portions, wherein the coating comprises a first composition, wherein the first composition comprises a first hair colouring agent, a hydrophobic phase, a hydrophilic phase, a surfactant, and an associative thickening polymer capable of interacting with the hydrophobic phase and the hydrophilic phase; and subsequently
 (ii) the formation of a second plurality of coated hair fibre portions, wherein the coating comprises a second composition, wherein the second composition comprises a second hair colouring agent, a hydrophobic phase, a hydrophilic phase, a surfactant, and an associative thickening polymer capable of interacting with the hydrophobic phase and the hydrophilic phase; and subsequently
 (iii) optionally, the formation of a third, optionally also a fourth, optionally also a fifth, optionally also a sixth plurality of coated hair fibre portions, wherein each coating comprises a composition, wherein the composition comprises a hair colouring agent, a hydrophobic phase, a hydrophilic phase, a surfactant, and an associative thickening polymer capable of interacting with the hydrophobic phase and the hydrophilic phase; and subsequently
 (iv) styling the hair wherein the pluralities of coated hair fibre portions are contacted with one another;
wherein the method does not comprise the application of a solid barrier means in order to separate the pluralities of coated hair fibre portions from each other, and wherein the associative thickening polymer comprises a hydrophilic backbone comprising acrylates groups, and wherein at least the first composition and/or second composition is substantially free of persulfate. In an embodiment, all compositions are substantially free of persulfate. In an embodiment, both the first and second compositions are substantially free of persulfate and both the first composition and second composition have a storage modulus of at least about 3000 Pa, or 3300 Pa, or 3500 Pa, or 4000 Pa, or 4500 Pa, or 5000 Pa, measured by frequency sweep at an angular frequency of 0.6 rad/s at 23° C.

An alternative method that does not fall within the scope of the first aspect as described herein, relates to method for colouring hair, wherein the method comprises:
 (i) the formation of a first plurality of coated hair fibre portions, wherein the coating comprises a first composition comprising a first hair colouring agent and an associative thickening polymer; and subsequently
 (ii) styling the hair wherein the first plurality of coated hair fibre portions is not substantially contacted with a second plurality of hair fibre portions;
and wherein the method does not comprise the application of a solid barrier means in order to separate the first plurality of coated hair fibre portions from the second plurality of hair fibre portions. In an embodiment of this alternative method, the first plurality of coated hair fibre portions may be styled to form spikes and/or knots. This alternative method is particularly suited to shorter hair. In an embodiment, the method comprises subsequent to the formation of the first plurality of coated hair fibre portions, the formation of a second plurality of coated hair fibre portions, wherein the coating on the second plurality of coated hair fibre portions comprises a second composition comprising a second hair colouring agent and an associative thickening polymer. In an embodiment, the second plurality of coated hair fibre portions may be styled to form spikes and/or knots.

"Not substantially contacted with", as used herein, means not purposefully placing two elements in close proximity such that they touch each other or not allowing two elements to be in close proximity such that they touch each other. In an embodiment of this alternative method when the first plurality of coated hair fibre portions is not substantially contacted with a second plurality of hair fibre portions, the first plurality of hair fibre portions ideally does not touch the second plurality of hair fibre portions. However, small and insignificant parts of the first plurality of hair fibre portions may touch the second plurality of hair fibre portions.

According to the second aspect, the present invention relates to composition for colouring hair comprising a hair colouring agent, a hydrophobic phase, a hydrophilic phase, a surfactant, and a thickener capable of interacting with the hydrophobic phase and the hydrophilic phase, wherein the composition has a storage modulus of at least about 3000 Pa, or at least about 3300 Pa, or at least about 3500 Pa, or at least about 4000 Pa, or at least about 4500 Pa, or at least about 5000 Pa, measured by frequency sweep at an angular frequency of 0.6 rad/s at 23° C., and wherein the thickener is an associative thickening polymer and comprises hydrophobic moieties and hydrophilic moieties. In an embodiment, the storage modulus is not more than 10 kPa, or 9 kPa, or 8 kPa, or 7 kPa, or 6 kPa, measured by frequency sweep at an angular frequency of 0.6 rad/s at 23° C. In an embodiment, the hydrophilic moieties comprise urethane units.

An alternative embodiment of the second aspect relates to a composition for colouring hair comprising a hair colouring agent, a hydrophobic phase, a hydrophilic phase, a surfactant, and a thickener capable of interacting with the hydrophobic phase and the hydrophilic phase, wherein the composition has a tangent delta of about 0.68 or less, alternatively about 0.66 or less, alternatively about 0.65 or less, alternatively about 0.64 or less, alternatively about 0.63 or less, alternatively about 0.62 or less, alternatively about 0.61 or less, alternatively about 0.60 or less, alternatively about 0.58 or less, measured by frequency sweep at an angular frequency of 0.6 rad/s at 23° C. and wherein the thickener is an associative thickening polymer and comprises hydrophobic moieties and hydrophilic moieties. Tangent delta=tan δ=loss factor. In an embodiment, the composition of this alternative embodiment also has a storage modulus of at least about 3000 Pa, or at least about 3300 Pa, or at least about 3500 Pa, or at least about 4000 Pa, or at least about 4500 Pa, or at least about 5000 Pa, measured by frequency sweep at an angular frequency of 0.6 rad/s at 23° C. In an embodiment, the storage modulus and/or tangent delta as described herein is measured using a TA-Instruments AR2000 rheometer. The details disclosed herein in relation to the first and/or second composition of the first aspect, are also applicable to the second aspect.

According to the third aspect, the present invention relates to the use of the composition according to the second aspect, for colouring and/or styling hair. The details disclosed herein in relation to the compositions of the first and second aspects, are also applicable to the third aspect.

According to the fourth aspect, the present invention relates to a kit comprising: (a) application instructions comprising the method according to the first aspect; (b) a composition. In an embodiment, the composition is selected from the group consisting of: the first composition as described herein (see first aspect); the thickening formulation as described herein (see seventh aspect). In an embodiment, the kit further comprises the second composition as described herein (see first aspect), which is packaged separately from the first composition. In an embodiment, the kit comprises: (a) application instructions comprising the method according to the first aspect; (b) a product comprising the first composition as described herein; (c) a product comprising the second composition as described herein. In an embodiment, the kit further comprises one or more of the following: (d) an implement; (e) a device. The details disclosed above in relation to the compositions of the first and second aspects, are also applicable to the fourth aspect.

According to the fifth aspect, the present invention relates to a process for creating a composition for colouring hair comprising mixing: a hair colouring agent; a hydrophobic phase; a hydrophilic phase; a surfactant; and a thickener capable of interacting with the hydrophobic phase and the hydrophilic phase; wherein the composition has a storage modulus of at least about 3000 Pa, or at least about 3300 Pa, or at least about 3500 Pa, or at least about 4000 Pa, or at least about 4500 Pa, or at least about 5000 Pa, measured by frequency sweep at an angular frequency of 0.6 rad/s at 23° C. In an embodiment of the fifth aspect, the thickener is an associative thickening polymer as described herein. The details disclosed above in relation to the compositions and formulations of the other aspects, are also applicable to the fifth aspect.

According to the sixth aspect, the invention relates to a method for demonstrating the immiscibility of two liquids, wherein the liquids exhibit different colours, the method comprising: (I) providing a first colour formulation, wherein the first colour formulation comprises a hydrophilic phase, a first colourant and an alkalising agent; (II) providing a second formulation, wherein the second formulation comprises a hydrophilic phase, a second colourant and an alkalising agent; (III) providing a thickening formulation, wherein the thickening formulation comprises thickener capable of interacting with the hydrophilic phase and capable of undergoing hydrophobic-hydrophobic interactions; (IV) mixing the first formulation with the thickening formulation to form a first liquid exhibiting a first colour and mixing the second formulation with the third formulation to form a second liquid exhibiting a second colour; (VI) applying the first liquid and second liquid next to each other in or on a receptacle; (VII) agitating the receptacle; (VIII) observing the immiscibility of the first composition and the second composition; (IX) optionally comparing said receptacle with a control demonstration where said liquids are devoid of said thickener. By "immiscibility" the liquids do not merge, mix or combine such that a third liquid exhibiting a third colour is observable. This method of demonstrating the immiscibility is used to demonstrate the efficacy of the method according to the first aspect in preventing staining. A technical effect of the method of the sixth aspect is demonstrating the effect of the thickener in preventing two different colourants from mixing. In an embodiment of the sixth aspect, the first liquid is the first composition according to the first aspect as described herein and the second liquid is the second composition according to the first aspect as described herein. In an embodiment, steps (I) to (III) can occur in any order so long as they preceed step (IV). The details disclosed herein in relation to the compositions and formulations of the other aspects, are also applicable to the sixth aspect.

According to the seventh aspect, the invention relates to a thickening formulation comprising: an oxidising agent, and an associative thickening polymer capable of interacting with a hydrophobic phase and a hydrophilic phase; and wherein the associative thickening polymer comprises hydrophobic moieties and hydrophilic moieties; and wherein the thickening formulation comprises at least 1.2% of associative thickening polymer; and wherein the thickening formulation comprises from about 1% to about 12% of an oxidising agent. In an embodiment, the oxidising agent is hydrogen peroxide; and wherein the hydrophilic moieties are selected from the group consisting of: urethane units, acrylate units, and mixtures thereof. In an embodiment, the thickening formulation comprises a thickener capable of interacting with the hydrophobic phase and the hydrophilic phase, wherein the thickening formulation comprises from about 0.001% to about 10.0%, or from about 0.01%, or 0.05%, or 0.1%, or 0.15%, or 0.25%, or 0.6%, or 1%, or 2%, or 2.5% to about 8%, or 7%, or 6%, or 5%, or 4%, or 3%, or 2%, or 1%, by total weight of the thickening formulation. The thickening formulation may further comprise an oxidising agent and the oxidising agent may be hydrogen peroxide. In an embodiment, a thickening formulation comprises from about 2%, or 3%, or 4%, or 4.5%, or 5% or 5.5%, or 6% to about 12%, or 10%, or 9%, or 8%, or 7% of an oxidising agent, by total weight of the thickening formulation. In an embodiment, a thickening formulation comprises a fatty alcohol, wherein the thickening formulation comprises from about 0.1%, or 0.5%, or 1%, or 2%, or 2.5% or 3%, to about 10%, or 9%, or 8%, or 7%, or 6%, or 5%, or 4% of fatty alcohol, by total weight of the thickening formulation. In an embodiment, the fatty alcohol is selected from the group consisting of cetyl alcohol, stearyl alcohol, cetearyl alcohol, behenyl alcohol, and mixtures thereof. In an embodiment, a thickening formulation comprises castor oil. In an embodiment, the thickening formulation comprises from about 0.1% to about 1% castor oil. In an embodiment, the castor oil is PEG hydrogenated castor oil. The details disclosed herein in relation to the thickening formulation mentioned with regard to the first aspect, are also applicable to the seventh aspect.

EXAMPLES

The following examples are colour formulations, developing formulations and thickening formulations for obtaining first and/or second compositions as described herein.

Colour formulations A to P

| Colour Formulation | Colour result | Hair colouring agent | Dye and salt load | Alkalising agent § | Other components § |
|---|---|---|---|---|---|
| A | black | Oxidative dye compounds | highest dye load, high electrolyte | low ammonia and MEA | Hydrophobic phase comprising hydrophobic components (20% to 28%); hydrophilic phase comprising water (50% to 76%); surfactant (4% to 6%); and alkalising agent(s) (3% to 11%). |
| B | neutral dark brown | Oxidative dye compounds | medium high dye load | medium low ammonia | |
| C | neutral light blond | Oxidative dye compounds | low dye load | high ammonia | |
| D | light brown e.g. hazelnut | Oxidative dye compounds | medium dye load | medium ammonia | |
| E | intense red shade | Oxidative dye compounds | high concentration of the dye pyrazole | high ammonia | |
| F | intense red shade | Oxidative dye compounds | low concentration of the dye pyrazole | high ammonia | |
| G | gold blond | Mixture of oxidative dye compounds and direct dyes | low dye load | high ammonia | |
| H | intense red shade | Direct dyes | high dye load | — | Hydrophilic phase, surfactant |
| I | gold shade | Direct dyes | low dye load | — | |
| J | Any of colour formulations A to G | Oxidative dye compounds | As per selected colour formulations A to G | 3% to 11% ammonia | Hydrophobic phase comprising hydrophobic components (8 to 10%); hydrophilic phase comprising water (75 to 90%); surfactant (2% to 3%). |
| K | Any of colour formulations A to G | Oxidative dye compounds | As per selected colour formulations A to G | 3% to 11% ammonia | Hydrophobic phase comprising hydrophobic components (2 to 10%); hydrophilic phase comprising water (75 to 95%); surfactant (1% to 3%). |
| L | Any of colour formulations A to G | Oxidative dye compounds | As per selected colour formulations A to G | 4 to 8% MEA | Hydrophobic phase comprising hydrophobic components (8 to 12%); hydrophilic phase comprising water (70 to 85%); surfactant (6% to 8%). |
| M | Optionally any of colour formulations A to G | Persulfate and optionally oxidative dye compounds | Optionally as per selected colour formulations A to G. | Up to 2% ammonia | Powder. |
| N | Any of colour formulations A to G | Oxidative dye compounds | As per selected colour formulations A to G | 3% to 11% ammonia | Hydrophobic phase comprising hydrophobic components (30 to 45%); hydrophilic phase comprising water (40 to 64%); surfactant (6% to 15%). |
| O | Any of colour formulations H to I | Oxidative dye compounds | As per selected colour formulations H to I | — | Hydrophobic phase comprising hydrophobic components (30 to 45%); hydrophilic phase comprising water (40 to 65%); surfactant (6% to 15%). |
| P | Any of colour formulations G | Mixture of oxidative dye compounds and direct dyes | As per colour formulation G | MEA | Hydrophobic phase comprising hydrophobic components (30 to 45%); hydrophilic phase comprising water (40 to 65%); surfactant (6% to 15%). |

KEY:
§ = stated numbers are percent calculated by w/w of the colour formulation.

| Developing Formulations I to V | | |
|---|---|---|
| Developing Formulation | Concentration of oxidising agent [§] | Other components [§] |
| I | 1% | Hydrophobic phase comprising cetearyl alcohol (2% to 6 %); surfactant (0.6% to 0.8%); hydrophilic phase comprising water (93% to 97%) |
| II | 4% | |
| III | 6% | |
| IV | 9% | |
| V | 12% | |

KEY:
[§] = stated numbers are percent calculated by w/w of the developing formulation.

| Thickening Formulations 1 to 6[§] | | | | | | |
|---|---|---|---|---|---|---|
| Component | 1 | 2 | 3 | 4 | 5 | 6 |
| ViscUP ® EZ[1] | — | — | — | 100 | — | — |
| Structure ® 3001[2] | 5.45 | — | — | — | 60 | 60 |
| Luvigel Star[3] | — | 90 | — | — | — | — |
| Aculyn 28[4] | — | — | 90 | — | — | — |
| Hydrogen peroxide (50%) | 12 | — | — | — | — | 1 |
| 1,2 Propylene Glycol | — | — | — | — | — | 2 |
| Cetearyl Alcohol | 3.4 | — | — | — | — | — |
| Cremophor A 25[5] | 0.80 | — | — | — | — | — |
| Salicylic Acid USP | 0.10 | — | — | — | — | — |
| Disodium Phosphate | 0.08 | — | — | — | — | — |
| Phoshoric Acid | 0.095 | — | — | — | — | — |
| Etidronic Acid (60%) | 0.01 | — | — | — | — | — |
| Methylparapen | — | — | — | — | — | 0.2 |
| Benzyl Alcohol | — | 0.4 | 0.4 | — | 0.4 | 0.4 |
| PEG Hydrogenated Castor Oil | — | 0.3 | 0.3 | — | 0.3 | — |
| Phenoxyethanol | — | 0.2 | 0.2 | — | 0.2 | — |
| Water | QSP | QSP | QSP | — | QSP | QSP |
| Total | 100 | 100 | 100 | 100 | 100 | 100 |

KEY:
[§] = stated numbers are percent calculated by w/wt of the thickening formulation;
[1] = comprises 45% active being a Sodium Acrylate/Sodium Acryloyldimethyl Taurate Copolymer, Hydrogenated Polydecene, Sorbitan Laurate, and Trideceth-6, and is available from Arch Personal Care Products;
[2] = comprises 30% active being Acrylates/Ceteth-20 Itaconate Copolymer from AkzoNobel;
[3] = comprises 20% active being Polyurethane-39 from BASF;
[4] = comprises 20% active being Acrylates/Beheneth-25 Methacrylate Copolymer from Rohm & Haas;
[5] = ceteareth-25 (inci name), PEG-25 Cetylstearylether (chemical name).

A selected colour formulation, selected developing formulation and selected thickening formulations are mixed together for obtaining first and/or second etc compositions as described herein. A hairstyle may then be created.

Hairstyle: Turban

Compositions pursuant to the present invention suitable for the turban hairstyle include, for example, a first composition comprising a colour formulation D, developing formulation III, and thickening formulation 5; combined with a composition comprising colour formulation G, developing formulation IV, and thickening formulation 5; and combined with a second composition comprising colour formulation C, developing formulation IV, and thickening formulation 5.

Figure 22:
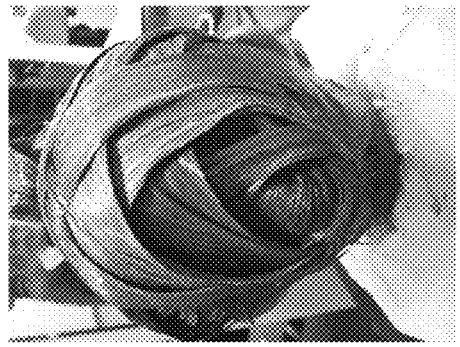
FIG. 22: Shows a turban hairstyle created by the method of the first aspect.
Figure 21:
FIG. 21: Shows a hairstyle created by the method of the first aspect.
Figure 20:
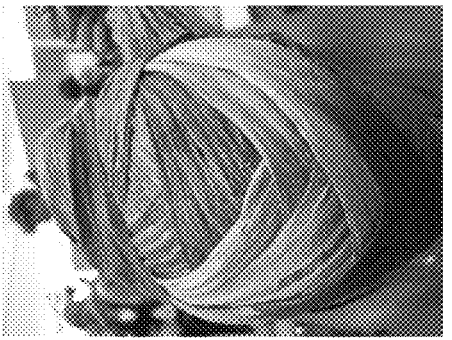
FIG. 20: Shows a turban hairstyle created by the method of the first aspect.
Figure 25:
FIG. 25: Shows a sculpting hairstyle created by the method of the first aspect.
Figure 24:
FIG. 24: Shows a sculpting hairstyle created by the method of the first aspect.

Method: Start applying the composition(s) on the top of the head downwards to the neck, finally the front of the head. The size of the plurality of hair fibre portions and application of the first, second and further compositions can vary as preferred/required. Apply the composition on the roots, lengths and ends directly and build a turban (see FIGS. 20, 21, 22). A plurality of hair fibre portions in this case is a plurality of hair fibres from root to tip originating from substantially the same roots. Each plurality of hair fibre portions can be applied with a different composition e.g. with a different resulting hair colour. Lie the plurality of hair fibre portions, depending on hair length, substantially flat on the top or on the back of the head. The hair is left for a development time suitable for the compositions chosen.

Hairstyle: Blending

Compositions pursuant to the present invention suitable for the blending hairstyle include, for example, a first composition comprising a colour formulation B, developing formulation III, and thickening formulation 5; combined with a second composition comprising colour formulation E, developing formulation III, and thickening formulation 5.

Figure 28:
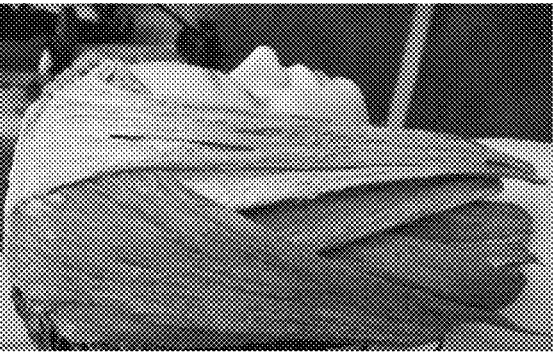
FIG. 28: Shows a blending hairstyle created by the method of the first aspect.

Method: A plurality of hair fibre portions in this case is a not a plurality of hair fibres from root to tip, but instead only a portion thereof e.g. the root portion, or the tip portion. Coloring the roots: Start colouring the roots on the top of the head downwards to the neck and finally the front of the head. Use thin pluralities of hair fibre portions and apply composition on the roots but only on a portion most proximal to the scalp. The extend of the portion proximal to the scalp should be decided upon i.e. how many cm of the roots to colour, e.g. 1 cm to 10 cm. Coloring lengths and ends: Now apply the composition on the lengths and ends directly afterwards—above and below. Apply the composition also onto the already coloured roots. Comb the plurality of hair fibre portions through to get a nice colour flow from root to tips. The blending hairstyle is shown in FIG. 28

Hairstyle: Criss-Cross

Compositions pursuant to the present invention suitable for the criss-cross hairstyle include, for example, a first composition comprising a colour formulation G, developing formulation IV, and thickening formulation 5; combined with a second composition comprising colour formulation D, developing formulation III, and thickening formulation 5; and combined with a third composition comprising colour formulation C, developing formulation IV, and thickening formulation 5.

Figure 23:
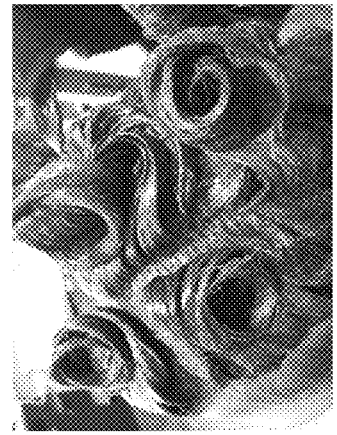
FIG. 23: Shows a criss-cross hairstyle created by the method of the first aspect.
Figure 26:
FIG. 26: Shows a criss-cross hairstyle created by the method of the first aspect.

Method: Start the colouring process at the neck and continue upwards to the top of the head. The plurality of hair fibre portions should be slice-like in shape and these slices should have a thickness of about 0.5 cm to 1 cm, as they are applied diagonally like as triangle. The compositions are applied from root to tip immediately, slice by slice. Each slice can become coated in a different composition according to the present invention, particularly differing by hair colouring agent, more preferably differing by resulting hair colour. All coloured slices lie over each other backwards, without additional pressure. The cross-cross hairstyle is shown in FIGS. 23 and 26. Development time is normally about 30 min without application of heat i.e. at room temperature.

Hairstyle: 2-Step

Compositions pursuant to the present invention suitable for the 2-step hairstyle include, for example, a first composition comprising a colour formulation E, developing formulation III, and thickening formulation 5; and combined with colour formulation M+developing formulation III.

Figure 27:
FIG. 27: Shows a 2-step hairstyle created by the method of the first aspect.

Method: A first composition is applied to the whole head of hair i.e. the plurality of hair fibre portions is the entire head of hair. However, selected pluralities of hair fibre portions then receive a second composition applied on top of the first composition. The 2-step may be leveraged to apply highlights via light-coloured dyes or bleaching on a formed hair shape created after styling the hair following application of the first composition. For example, curls can be created using the sculptability of the first composition, and then the light-coloured dye/bleach is applied onto the outer surface of the curl. The light coloured dye may be the second composition as described herein. First, using the first composition, start application on the top of the head downwards to the neck, finally the front of the head. Afterwards create some sculpted constructs using creativity, e.g. a water wave, a twister, a braid the hair. Choose a brush or special applicator to apply the light-coloured dye/bleach, e.g. a thin brush. Start applying the light-coloured dye/bleach on the "constructs" as desired. The 2-step hairstyle is shown in FIG. 27

Data

Experiment 1—Rheology Measurements

In this experiment, different compositions pursuant to the present invention, which differed in the specific thickener used, were compared with a compositions not pursuant to the present invention. The time-dependent viscoelastic properties in the linear viscoelastic region with a frequency sweep were measured and compared.

Apparatus:

Analytical balance, top loading, precision 0.01 g (Mettler) or equivalent; Applicator brush and bowl or equivalent; Stopwatch capable of measuring 5 min to 1 s display; Advanced Rheometer (TA-Instruments AR2000 or AR2000ex) or equivalent.

Sample Preparation:

Place the bowl on the balance, tare and add 30 g (±1 g) of Tint. Record the weight, tare again and add the same amount of developer (±0.1 g). Using the brush, mix the sample for 10 seconds. Tare the balance again and add 3 g of thickener and mix for 1 Minute. Let the mixture develop for 4 minutes and then load it onto the Rheometer.

Frequency Sweep:

The composition is placed between two rheometer plates and an oscillatory shear stress is applied resulting in an oscillatory strain response of 0.05%, while the angular frequency is increased stepwise from 0.1 rad/s to 10 rad/s. The relationship between the sinusoidal stress applied and the resulting strain response as well as the shift between both measures on the time axis are monitored.

Frequency sweep: 40 mm flat acrylic plate; Peltier plate; Geometry Gap: 1000 μm; Temperature: 23; Conditioning in the instrument: 60 s.

Reporting results: For the frequency sweep the storage modulus [G'], loss modulus [G"], loss factor [tan δ] are reported.

Experiment 1—Compositions Tested

The following compositions were tested in Experiment 1.

| Composition ID | Colour Formulation* | Developing Formulation* | Thickening Formulation* | Mixing ratio (by weight) as Colour Formulation: Developing Formulation: Thickening Formulation | Amount of thickener[#] in composition |
|---|---|---|---|---|---|
| [a] | A | III | — | 10:10:0 | — |
| [c] | A | III | 5 | 10:10:1 | 0.86 |
| [e] | A | III | 2 | 10:10:1 | 0.86 |
| [d] | A | III | 3 | 10:10:1 | 0.86 |
| [b] | A | III | 4 | 10:10:0.83 | 1.73 |
| [k] | A | — | 1 | 10:0:10 | 0.82 |
| [f] | C | V | — | 10:10:0 | — |
| [h] | C | V | 5 | 10:10:1 | 0.86 |
| [j] | C | V | 2 | 10:10:1 | 0.86 |
| [i] | C | V | 3 | 10:10:1 | 0.86 |

-continued

| Composition ID | Colour Formulation* | Developing Formulation* | Thickening Formulation* | Mixing ratio (by weight) as Colour Formulation: Developing Formulation: Thickening Formulation | Amount of thickener[#] in composition |
|---|---|---|---|---|---|
| [g] | C | V | 4 | 10:10:0.83 | 1.73 |
| [l] | C | — | 1 | 10:0:10 | 0.82 |

*= see Examples section above;
[#]= thickener capable of interacting with the hydrophobic phase and the hydrophilic phase.

Compositions [a] and [f] are not pursuant to the present invention because they do not comprise a thickener capable of interacting with the hydrophobic phase and the hydrophilic phase. Consequently, compositions [a] and [f] are control compositions.

Experiment 1—Results

Figure 29:
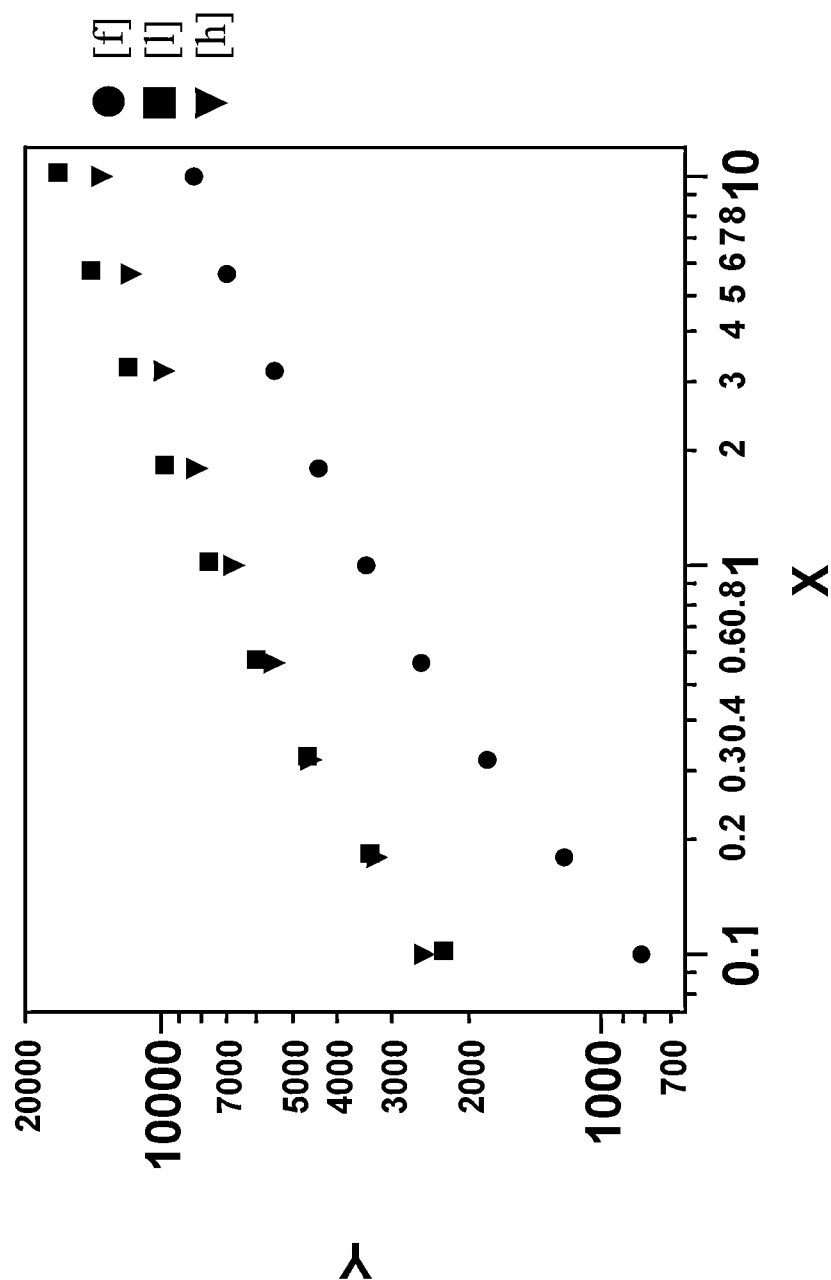
FIG. 29: Shows a rheology graph. X=angular frequency [rad/s]. Y=storage modulus, G' [Pa]. Compositions [f], [l] and [h] were tested—see "Experiment 1—Compositions tested" in the Data section below. Composition [f] is not pursuant to the present invention.
Figure 30:
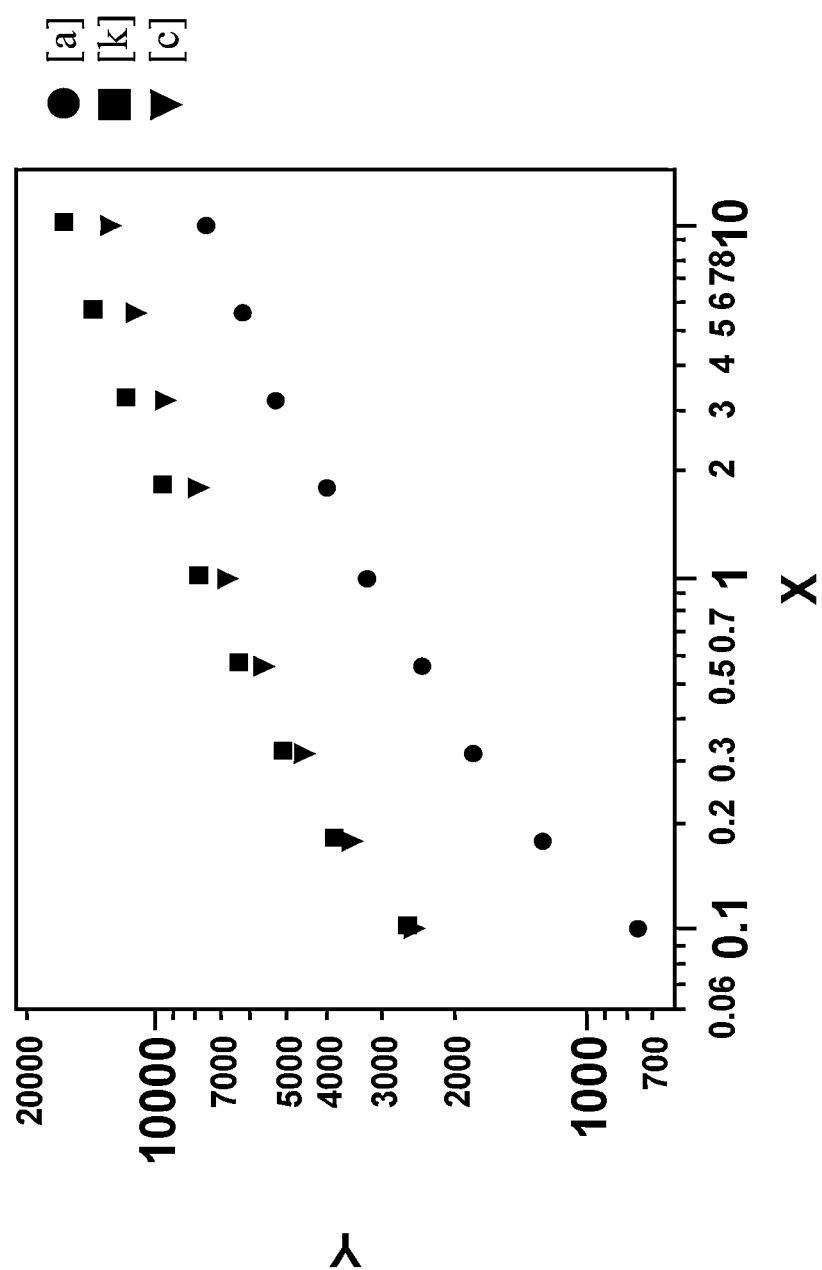
FIG. 30: Shows a rheology graph. X=angular frequency [rad/s]. Y=storage modulus, G' [Pa]. Compositions [a], [k] and [c] were tested—see "Experiment 1—Compositions tested" in the Data section below. Composition [a] is not pursuant to the present invention.

The results of the rheology experiments of experiment 1 are shown in FIGS. 12 to 19 and FIGS. 29 and 30. Conclusions from FIGS. 12 to 19 include that significant differences were found between the compositions pursuant to the present invention and the comparative compositions [a] and [f]. The data was also found to be highly reliable with a low standard deviation. The storage modulus relates to the elastic resistance of the composition against deformation and the loss factor the level of elasticity the composition possesses. These measurements substantiate the superior 'hold' demonstrated by the compositions pursuant to the present invention. FIGS. 29 and 30 show that there is little difference between compositions [1] and [h] (FIG. 29), and between [k] and [c] (FIG. 30). Thus, there is apparently little difference between the final composition created from the employment of thickening formulation 5 versus thickening formulation 1. Thickening formulation 1 has the advantage that the high concentration of oxidising agent present in this formulation negates the need for mixing in a third formulation—i.e. a separate developing formulation.

Experiment 2—Long-Lasting Hold Evaluation

Compositions [a] to [j] as used for experiment 1 were used to evaluate hold strength afforded. As in experiment 1 compositions [a] and [f] are not pursuant to the present invention because they do not comprise a thickener capable of interacting with the hydrophobic phase and the hydrophilic phase. Consequently, compositions [a] and [f] are control compositions. The long lasting hold measurements are observations of the height changes of hair tresses over time at elevated humidity (20° C. and a humidity of 65% relative humidity). These methods are performed in order to determine the form stability i.e. the amount of hold, of hair tresses treated with the compositions pursuant to the present invention. With a height calliper comprising a laser, the height changes of tresses are detected, which indicate the amount of hold provided by the compositions pursuant to the present invention. The following method was used:

Treatment with Each Composition:

A total of at least 20 g of each composition [a] to [j] is thoroughly mixed using a colour brush or in an applicator flask. 5 dry tresses with a length of 170 mm and a dry weight of 2.00 g to 2.02 g are put on a Plexiglas plate. The composition is applied to the tresses. The composition is dispersed equally on the hair tress using a brush such that the hairs of the tress are kept brushed straight and parallel. The final weight of each tress is 6.20 g to 6.23 g.

Measurement Procedure:

The tresses each have a rubber gatherer at one end, and these rubber ends of the treated tresses are mounted horizontally on a rack. 55 mm in front of the rack is a narrow bar which is parallel and at the same height above the bench as the rack. Each tress lies horizontally from the rack to narrow bar. After the narrow bar a protruding length of 102 mm for each tress is left over. A wet tress (comprising 50% humidity, which would reflect towel dry hair) hangs down loosely from the narrow bar. The composition applied to the tresses provide stiffness (i.e. hold) to the protruding length of the tresses such that they do not hang down loosely from the narrow bar. The extent to which the protruding length of the tress is held is measured by measuring the height of the tip of the tress. The height projection of the tip end of the tress is determined by means of an altimeter with semiconductor laser immediate. The measurement is taken after 0 min, 10 min, and 30 min. Taking the length of the tress into account the resulting hold is calculated as follows:

$$\text{hold } [\%] = 100 - ((l_t/102) \times 100)$$

where $l_t$=height of horizontally projected tress and 102 mm=protruding length of the tress.

A tress that remained horizontal would have an $l_t$ of 0 mm, and therefore a percentage hold of 100% i.e. this would be the best possible result. A wet tress that hangs down loosely would have an $l_t$ of 102 mm, and therefore a percentage hold of 0% i.e. this would be the worst possible result.

The results of the hold evaluation are shown below. Each hold value is a mean of 5 repeats, since for every composition 5 tresses were utilised.

| Composition* | Hold after 0 mins | Hold after 10 mins | Hold after 30 mins |
| --- | --- | --- | --- |
| [a] | 9.86 | 8.00 | 7.85 |
| [c] | 16.85 | 13.16 | 10.97 |
| [e] | 15.77 | 10.80 | 9.25 |
| [d] | 27.16 | 13.71 | 11.24 |
| [b] | 17.41 | 12.50 | 10.61 |
| [f] | 6.67 | 5.90 | 5.24 |
| [h] | 12.85 | 8.30 | 7.07 |
| [j] | 9.72 | 5.83 | 5.14 |
| [i] | 17.68 | 9.93 | 8.35 |
| [g] | 13.73 | 9.24 | 7.64 |

*= see compositions tested in experiment 1.

Conclusions: The results for compositions [a], [b], [c], [d], and [e] can be compared with each other because the colour formulation used was the same. Compositions [b] to [e] provided a better hold than composition [a]. The results for compositions [f] to [j] can be compared with each other because the colour formulation used was the same. Compositions [h] to [j] provided a better hold than composition [f]. These data are relevant to stylists work. For example, the 0 min measurement is most relevant to the stylist's work because this occurs during the application phase i.e. when the composition is applied to the head of hair. Consequently these data are very realistic. The 10 min and 30 min measurements relate more to the development phase.

Experiment 3—Colour Migration Experiment

The colour migration experiment is an examination of the migration behaviour of colouring agents comprised in compositions pursuant and not pursuant to the present invention. For each experiment, a first composition is chosen, which comprises a first hair colouring agent, and a second composition is chosen, which comprises a second hair colouring agent being different to the first hair colouring agent. In order to achieve the boundary layer for the examination, the two compositions are applied immediately after mixing onto a microscope slide. After the desired development time the boundary layer between the two masses is visualized by using a digital camera system with macroscopic lens equipment. For avoiding gloss due to illumination, an integrating sphere with cold light source is used. After image capturing regions of interests (ROI) in the appropriate colour channel (R,G,B) around the boundary layer are defined for the calculation. For quantitative analysis, line profiles perpendicular to the layer with defined thickness of the ROIs are generated with image analysis software and can be used for calculating or visualizing the colour migration behavior. Line profiles are detecting the intensity value for each pixel over the entire length; thus the analysis of the gradient at the "layer zone" gives the information about the colour migration: the steeper the gradient between the average level of each colour, the less the colour migration from the first composition into the second composition. The qualitative results of the colour migration experiments are shown in FIGS. 1 to 11.

Conclusions from experiment 3 include: that solid barrier means are not required vis-à-vis the method of the first aspect. Compare FIGS. 1-7 versus FIGS. 8-11. The thickener as described in the present invention has the effect that a clear interface between the two compositions is observable that can be correlated with little or no staining.

Experiment 4—Stylist Assessments of Doll Heads

Four compositions pursuant to the present invention are provided. The colour formulations are colour formulations E, B, G and D. All four compositions are obtained by mixing developing formulation III and thickening formulation 5. All colour formulations comprise oxidative dye compounds. The mixing ratios of colour formulation:developing formulation:thickening formulation are 10:10:1. The criss-cross hairstyle is created on doll heads. On one half side of each doll head, a criss-cross hairstyle is created using a composition comprising colour formulation E (intense red), developing formulation III and thickening formulation 5; and a composition comprising colour formulation B (neutral dark brown), developing formulation III and thickening formulation 5. On the other side, a criss-cross hairstyle is created using a composition comprising colour formulation G (gold blond), developing formulation III and thickening formulation 5; and a composition comprising colour formulation D (light brown), developing formulation III and thickening formulation 5. A total of 3 doll heads are employed, each doll head is treated by a different stylist (i.e. a total of 3 stylists). The stylists who treat the doll heads, evaluate their experience during application and development time for below criteria.

| Criteria | Rating of 10 | Rating of 7 more | Rating or between 6.9 and 4.1 | Rating of 4 or less | Rating of 0 |
| --- | --- | --- | --- | --- | --- |
| Sculptability during application | Easy | excellent-good | good-acceptable | unacceptable | difficult |
| Hold during application | Strong | excellent-good | good-acceptable | unacceptable | weak |
| Ability to execute freehand application | Very safe feeling | excellent-good | good-acceptable | unacceptable | Unsafe feeling |

| Criteria | Rating of 10 | Rating of 7 more | Rating or between 6.9 and 4.1 | Rating of 4 or less | Rating of 0 |
|---|---|---|---|---|---|
| Hold during development time | Strong | excellent-good | good-acceptable | unacceptable | Weak |
| Stability of hair with applied color | Lasts complete development time | excellent-good | good-acceptable | unacceptable | Hair style collapses immediately |

In addition, after washing out the compositions and drying the hair, the results of the hair colouring are assessed by a total of 11 stylists for each half side of each doll head. 1 of the 10 stylists is the executor of the doll head colouring. The remaining 10 are blind assessors. Each stylist gives the doll head result a rating based on the below table.

| Criteria | Rating of 10 | Rating of 7 or more | Rating between 6.9 and 4.1 | Rating of 4 or less | Rating of 0 |
|---|---|---|---|---|---|
| Colour separation (overall rating) | Excellent separation overall | excellent-good | good-acceptable | unacceptable | No colour separation at all |
| Color separation (specific) | Excellent effect: true to tone of single hair fibre portion | excellent-good | good-acceptable | unacceptable | Base colour has completely changed (e.g. blond is now rose) |
| Colour spots | No spots at all | excellent-good | good-acceptable | unacceptable | Spots on all hair fibre portions |

The results of experiment 4 are shown in the following table.

| Criteria | Base Size of Stylist | Overall Mean Rating | Base Size for Red-Brown | Average Rating for Red-Brown | Base Size for Blond-Brown | Average Rating for Blond-Brown |
|---|---|---|---|---|---|---|
| Sculptability during application | 6 | 7.00 | 3 | 6.67 | 3 | 7.33 |
| Hold during application | 6 | 6.67 | 3 | 6.33 | 3 | 7.00 |
| Ability to execute freehand application | 6 | 6.83 | 3 | 6.67 | 3 | 7.00 |
| Hold during development time | 6 | 8.17 | 3 | 8.00 | 3 | 8.33 |
| Stability of hair with applied color | 6 | 9.58 | 3 | 9.50 | 3 | 9.67 |
| Colour separation (overall) | 66 | 7.86 | 33 | 7.99 | 33 | 7.73 |
| Color separation (specific) | 66 | 7.59 | 33 | 7.79 | 33 | 7.39 |
| Colour spots | 66 | 7.43 | 33 | 7.70 | 33 | 7.15 |

Conclusions from experiment 4: The stylists rated the effect of the compositions pursuant to the present invention consistently overall as good to excellent.

Experiment 5—Stylist Assessments of Live Models

Compositions pursuant to the present invention are prepared. The compositions as described herein are applied onto real heads of hair. The colour formulation (comprising a hair colouring agent) utilised to create the composition differed depends on the hairstyle to be created and a suitable developing formulation for the colour formulation is selected. A wide variety of hair colouring agents are chosen. The thickener chosen is thickening formulation 5 (see example section). The 1× blending hairstyle, 6× turban hairstyle and 1× painting hairstyle are created by stylists. After rinsing out the compositions from the hair and drying the hair, the stylists evaluate the colour result according to the below 5 point scale.

| Stylist rating | Meaning | Score |
|---|---|---|
| − − | no effect at all | 0 |
| − | slight effect | 25 |
| −/+ | medium good | 50 |
| + | good effect | 75 |
| + + | excellent effect | 100 |

Results:

| Criteria | Mean Score | Base size stylists | Base size models |
|---|---|---|---|
| Color Separation | 82 | 38 | 8 |
| Color Spots | 80.5 | 34 | 7 |
| Hold | 84 | 8 | 7 |
| Color Flow | 70 | 5 | 1 |

Conclusions from experiment 5 include: Excellent results were obtained for both the hairstyle created pursuant to the method described herein and also for the hair effects resulting from the method described herein.

Experiment 6—Comparison with Reduced Amount of Acrylates/Ceteth-20 Itaconate Copolymer Experiment 6(i) relates to the rheology measurement, carried out as per the methodology of Experiment 1 above, of a comparative composition gamma. Experiment 6(ii) relates to long-lasting hold evaluation of comparative composition gamma, wherein this experiment is carried out as per Experiment 2 above. The comparative composition gamma (γ) is created by mixing together a formula alpha (α) and a formula beta (β) at a 1:1 ratio.

| Component. | Formula Alpha | Formula Beta |
|---|---|---|
| Emersol 233LL fatty acid [1] | 35 | — |
| Tween 81 [2] | 10 | — |
| Arlacel 80 [3] | 3.5 | — |
| Atlas G-1411 [4] | 1.75 | — |
| Centrolene S [5] | 1.25 | — |
| Sequestrene AA [6] | 0.1 | — |
| Sodium Sulfite [7] | 0.5 | — |
| Ammonium Hydroxide (25%) [8] | 11.2 | — |
| 2-(methoxymethyl)-benzene-1,4-diamine [9] | 0.62 | — |
| Resorcinol [9] | 0.28 | — |
| Super D (35%) [10] | — | 16.7 |
| Structure 3001 [11] | — | 3.33 |

-continued

| Component. | Formula Alpha | Formula Beta |
|---|---|---|
| Phosphoric Acid | — | 0.1 |
| Water | QSP | QSP |
| Total | 100 | 100 |

KEY:
[1] = oleic acid;
[2] = Polysorbate 81
[3] = sorbitan oleate;
[4] = PEG-40 Sorbitan Lanolate;
[5] = Lecithin;
[6] = disodium ethylenediaminetetraacetate;
[7] = sodium sulfite;
[8] = Ammonia (25% aqueous solution);
[9] = oxidative dye compound;
[10] = hydrogen peroxide, 35% aqueous solution;
[11] = comprises 30% active being Acrylates/Ceteth-20 Itaconate Copolymer from AkzoNobel.

The amount of thickening active in composition beta is 1% and in composition gamma is thus 0.5%.

Figure 31:
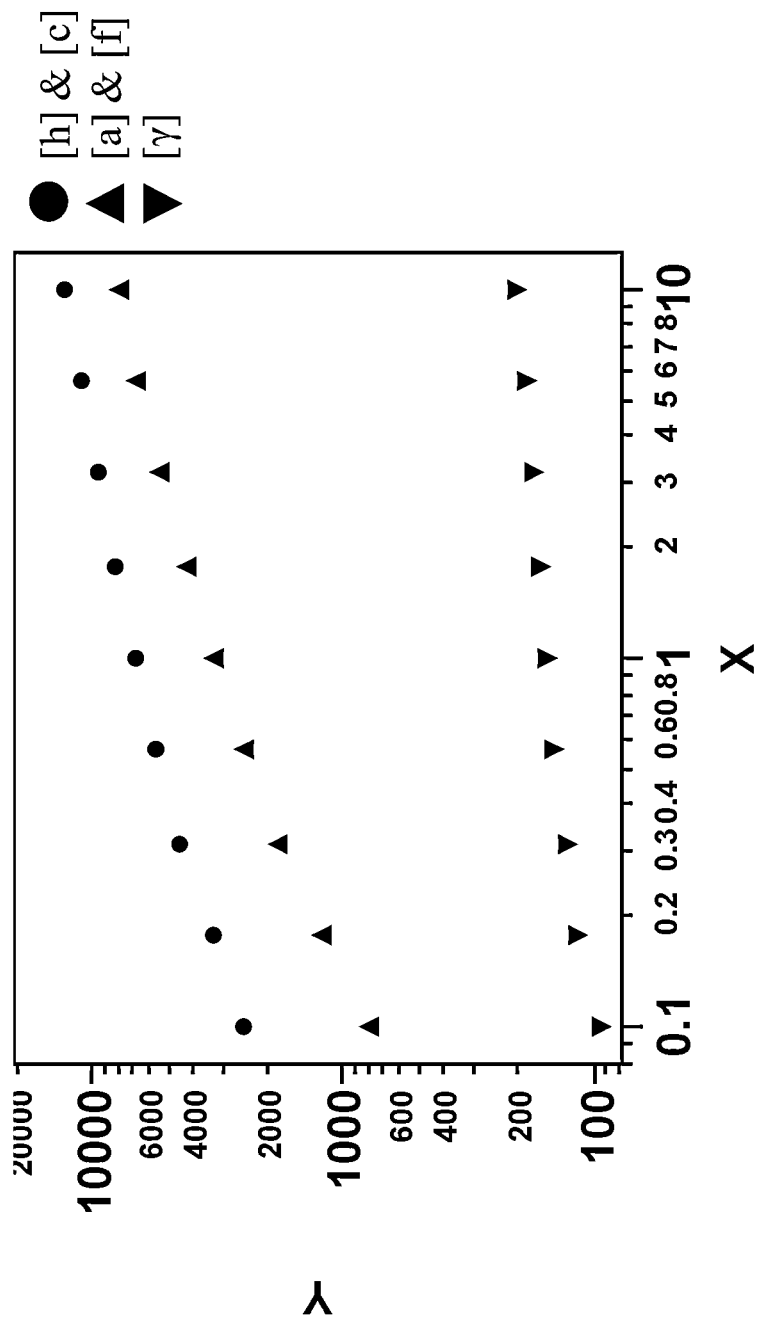
FIG. 31: Shows a rheology graph. X=angular frequency [rad/s]. Y=storage modulus, G' [Pa]. Compositions [h], [c], [f], [a] and [γ] were tested—see "Experiment 1—Compositions tested" and also "Experiment 6" in the Data section below. The mean storage modulus is shown for [h] and [c], and for [f] and [a]. Compositions [a] and [f] are not pursuant to the present invention. For composition [γ], the storage modulus is less than 3000 Pa measured by frequency sweep at an angular frequency of 0.60 rad/s at 23° C.
Figure 32:
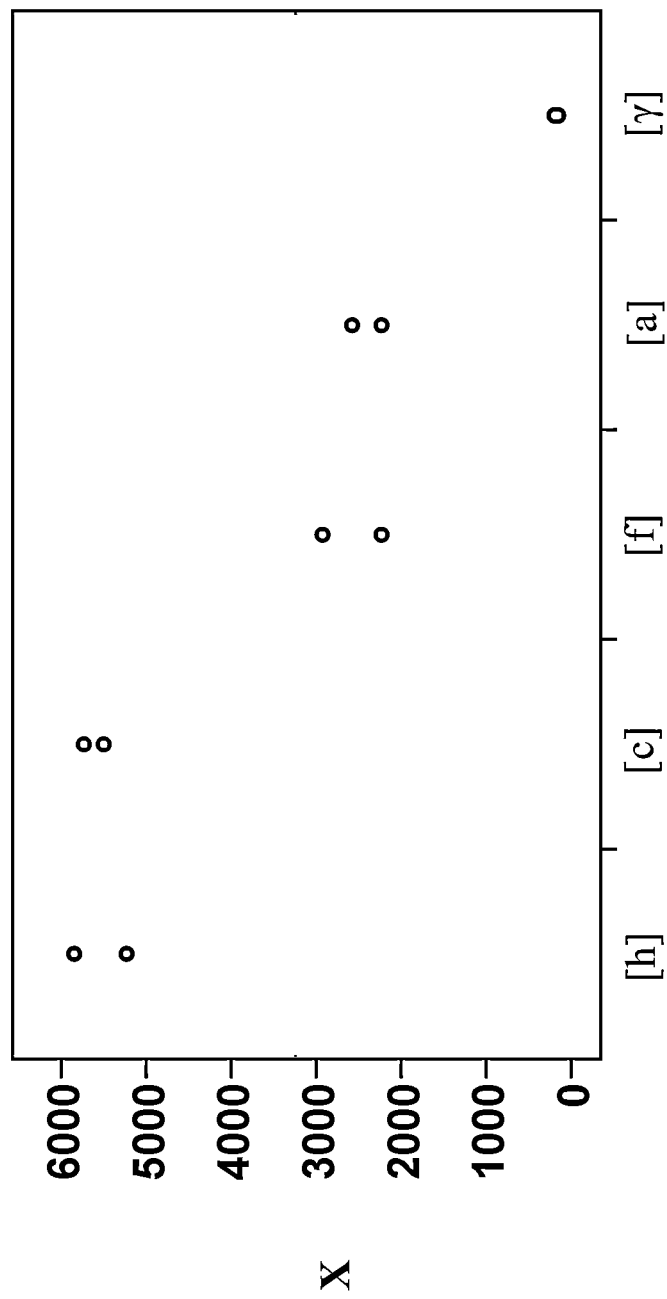
FIG. 32: Shows a rheology graph. X=storage modulus, G' [Pa]. Here, the storage modulus for compositions [h], [c], [f], [a] and [γ] measured by frequency sweep at an angular frequency of 0.56 rad/s at 23° C. is shown. For each composition, the measurement was taken twice and these are shown—hence two data points for each composition.

The results of the rheology experiments (experiment 6[i]) are shown in FIGS. 31 and 32. From these experiments it can be concluded that there is a significant difference in the rheology behaviour of composition gamma [γ] versus compositions [h] and [c]. Thus, composition gamma [γ] does not fall within the scope of the composition according to the second aspect since the storage modulus is well below 3000 Pa measured by frequency sweep at an angular frequency of 0.6 rad/s at 23° C.

The results of the hold evaluation (experiment 6[ii]) are shown below. Each hold value is a mean of 5 repeats, since for every composition 5 tresses were utilised.

| Composition* | Hold after 0 mins | Hold after 10 mins | Hold after 30 mins |
|---|---|---|---|
| [γ] | 8.75 | 5.89 | 3.11 |
| [h] | 33.20 | 14.43 | 10.69 |
| [c] | 17.43 | 11.03 | 9.00 |
| [a] | 5.67 | 4.82 | 3.80 |
| [f] | 8.13 | 6.83 | 4.54 |

*= see compositions tested in experiment 1.

The statistical significance of these data was analysed. Using a one-way ANOVA, it was found that the differences of [c] versus [γ] and [h] versus [γ] was significant. For [a] versus [γ], the difference was found to be significant. For [f] versus [γ], the difference was not found to be significant. In can thus be concluded that comparative composition [γ] provides significantly less hold than compositions comprising a higher concentration of thickener active.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for colouring hair, wherein the method comprises:
   forming a first plurality of coated hair fibre portions, wherein the coating comprises a first composition having a storage modulus of at least about 3,000 Pa as measured by frequency sweep at an angular frequency of 0.6 rad/s at 23° C., wherein the first composition comprises
   a first hair colouring agent,
   a hydrophobic phase,
   a hydrophilic phase comprising fatty alcohols and/or fatty acids with 10 to 30 carbon atoms,
   from about 0.5% to about 5% of a surfactant by weight of the first composition, and
   from about 0.6% to about 8% of a thickener by weight of the first composition, wherein the thickener is selected from the group consisting of acrylates/ceteth-20 itaconate copolymers, acrylates/C10-30 alkyl acrylate crosspolymers, sodium acrylate/sodium acryloyldimethyl taurate copolymers, and mixtures thereof, wherein the thickener is capable of interacting with the hydrophobic phase and the hydrophilic phase; and subsequently
   styling the hair during application of the first composition using spikes, braids, updos, twists, and/or knots, wherein the first plurality of coated hair fibre portions is contacted with a second plurality of hair fibre portions; and
   rinsing the composition from the hair
   wherein
   the method does not comprise the application of a solid barrier means in order to separate the first plurality of coated hair fibre portions from the second plurality of hair fibre portions,
   the first composition is substantially free of persulfate;
   forming the first plurality of coated hair fibre portions comprises applying the first composition to a first plurality of hair fibre portions, and
   the hair displays a colour effect following rinsing.

2. The method according to claim 1, comprising:
   forming the second plurality of coated hair fibre portions, wherein the coating comprises a second composition, wherein the second composition comprises
   a second hair colouring agent,
   a hydrophobic phase,
   a hydrophilic phase,
   a surfactant, and
   a thickener capable of interacting with the hydrophobic phase and the hydrophilic phase; and subsequently
   contacting the first plurality of coated hair fibre portions with the second plurality of coated hair fibre portions;
   wherein the second hair colouring agent is different from the first hair colouring agent.

3. The method according to claim 1, wherein the first and/or second hair colouring agent are oxidative dye compounds; and wherein the first and/or second composition comprises an oxidising agent.

4. The method according to claim 1, wherein the first composition has a storage modulus of at least about 4000 Pa measured by frequency sweep at an angular frequency of 0.6 rad/s at 23° C.

5. The method according to claim 1, wherein the surfactant is ceteareth-n wherein n is from about 10 to about 30.

6. The method according to claim 1, wherein the thickener is about 0.6 wt % to about 2 wt % of the first composition.

7. The method according to claim 1, wherein the thickener is an acrylates/ceteth-20 itaconate copolymer.

8. The method according to claim 7, wherein the acrylates/ceteth-20 itaconate copolymer thickener is about 0.6 wt % to about 1 wt % of the first composition.

9. The method according to claim 1, wherein the first composition has a storage modulus of at least about 5,000 Pa measured by frequency sweep at an angular frequency of 0.6 rad/s at 23° C.

10. The method according to claim 1, wherein the method further comprises application of a liquid barrier means to separate the first plurality of coated hair fibre portions from the second plurality of hair fibre portions.

11. A method for colouring hair, wherein the method comprises:
   forming a first plurality of coated hair fibre portions, wherein the coating comprises a first composition, wherein the first composition comprises
   a first hair colouring agent,
   a hydrophobic phase,
   a hydrophilic phase comprising fatty alcohols and/or fatty acids with 10 to 30 carbon atoms,
   from about 0.5% to about 5% of a surfactant by weight of the first composition, and
   from about 0.6% to about 2% of a thickener by weight of the first composition, wherein the thickener is selected from the group consisting of acrylates/ceteth-20 itaconate copolymers, acrylates/C10-30 alkyl acrylate crosspolymers, sodium acrylate/sodium acryloyldimethyl taurate copolymers, and mixtures thereof, wherein the thickener is capable of interacting with the hydrophobic phase and the hydrophilic phase; and subsequently
   styling the hair during application of the first composition using spikes, braids, updos, twists, and/or knots, wherein the first plurality of coated hair fibre portions is contacted with a second plurality of hair fibre portions; and
   rinsing the composition from the hair
   wherein
   the method does not comprise the application of a solid barrier means in order to separate the first plurality of coated hair fibre portions from the second plurality of hair fibre portions,
   the first composition is substantially free of persulfate,
   the first composition has a storage modulus of at least about 5,000 Pa measured by frequency sweep at an angular frequency of 0.6 rad/s at 23° C.; and
   forming the first plurality of coated hair fibre portions comprises applying the first composition to a first plurality of hair fibre portions, and
   the hair displays a colour effect following rinsing.

12. The method of claim 11, wherein the thickener is an acrylates/ceteth-20 itaconate copolymer.

* * * * *